US007822452B2

(12) United States Patent
Schurman et al.

(10) Patent No.: US 7,822,452 B2
(45) Date of Patent: Oct. 26, 2010

(54) METHOD FOR DATA REDUCTION AND CALIBRATION OF AN OCT-BASED BLOOD GLUCOSE MONITOR

(75) Inventors: Matthew J. Schurman, Somerset, NJ (US); Walter J. Shakespeare, Macungie, PA (US); William Henry Bennett, Bethlehem, PA (US)

(73) Assignee: GLT Acquisition Corp., Irvine, CA (US)

( * ) Notice: Subject to any disclaimer, the term of this patent is extended or adjusted under 35 U.S.C. 154(b) by 1171 days.

(21) Appl. No.: 11/403,635

(22) Filed: Apr. 13, 2006

(65) Prior Publication Data

US 2006/0264719 A1 Nov. 23, 2006

Related U.S. Application Data

(63) Continuation-in-part of application No. 10/916,236, filed on Aug. 11, 2004, now Pat. No. 7,254,429.

(60) Provisional application No. 60/671,007, filed on Apr. 13, 2005, provisional application No. 60/671,285, filed on Apr. 14, 2005.

(51) Int. Cl.
*A61B 5/1455* (2006.01)
(52) U.S. Cl. .................................... 600/316
(58) Field of Classification Search ................. 600/310, 600/316, 322, 473, 476
See application file for complete search history.

(56) References Cited

U.S. PATENT DOCUMENTS

| 3,826,905 A | 7/1974 | Valkama et al. |
| 3,958,560 A | 5/1976 | March |
| 4,014,321 A | 3/1977 | March |
| 4,476,875 A | 10/1984 | Nilsson et al. |
| 4,590,948 A | 5/1986 | Nilsson |
| 4,606,351 A | 8/1986 | Lubbers |

(Continued)

FOREIGN PATENT DOCUMENTS

EP 0282234 9/1988

(Continued)

OTHER PUBLICATIONS

Arnold, M.A. et al., "Determination of Physiological Levels of Glucose in an Aqueous Matrix with Digitally Filtered Fourier Transform Near-Infrared Spectra," Anal. Chem. 64(14):1457-64 (1990).

(Continued)

*Primary Examiner*—Eric F Winakur
*Assistant Examiner*—Etsub D Berhanu
(74) *Attorney, Agent, or Firm*—Knobbe, Martens, Olson & Bear, LLP

(57) ABSTRACT

The present invention relates to a method for estimating blood glucose levels using a noninvasive optical coherence tomography- (OCT-) based blood glucose monitor. An algorithm correlates OCT-based estimated blood glucose data with actual blood glucose data determined by invasive methods. OCT-based data is fit to the obtained blood glucose measurements to achieve the best correlation. Once the algorithm has generated sets of estimated blood glucose levels, it may refine the number of sets by applying one or more mathematical filters. The OCT-based blood glucose monitor is calibrated using an Intensity Difference plot or the Pearson Product Moment Correlation method.

41 Claims, 11 Drawing Sheets

U.S. PATENT DOCUMENTS

| | | | |
|---|---|---|---|
| 4,655,225 A | 4/1987 | Dahne et al. |
| 4,704,029 A | 11/1987 | Van Heuvelen |
| 4,731,363 A | 3/1988 | Hamilton et al. |
| 4,743,604 A | 5/1988 | Alig et al. |
| 4,750,830 A | 6/1988 | Lee |
| 4,834,111 A | 5/1989 | Khanna et al. |
| 4,871,755 A | 10/1989 | Alig et al. |
| 4,873,989 A | 10/1989 | Einzig |
| 4,882,492 A | 11/1989 | Schlager |
| 4,883,953 A | 11/1989 | Koashi et al. |
| 4,890,621 A | 1/1990 | Hakky |
| 4,901,728 A | 2/1990 | Hutchinson |
| 4,948,248 A | 8/1990 | Lehman |
| 4,960,128 A | 10/1990 | Gordon et al. |
| 4,964,408 A | 10/1990 | Hink et al. |
| 4,979,509 A | 12/1990 | Hakky |
| 4,989,978 A | 2/1991 | Groner |
| 5,025,785 A | 6/1991 | Weiss |
| 5,028,787 A | 7/1991 | Rosenthal et al. |
| 5,041,187 A | 8/1991 | Hink et al. |
| 5,054,487 A | 10/1991 | Clarke |
| 5,069,213 A | 12/1991 | Polczynski |
| 5,070,874 A | 12/1991 | Barnes et al. |
| 5,101,814 A | 4/1992 | Palti |
| 5,112,124 A | 5/1992 | Harjunmaa et al. |
| 5,115,133 A | 5/1992 | Knudson |
| 5,163,438 A | 11/1992 | Gordon et al. |
| 5,168,325 A | 12/1992 | Yoder-Short |
| 5,178,153 A | 1/1993 | Einzig |
| 5,209,231 A | 5/1993 | Cote et al. |
| 5,222,495 A | 6/1993 | Clarke et al. |
| 5,222,496 A | 6/1993 | Clarke et al. |
| 5,243,983 A | 9/1993 | Tarr et al. |
| 5,267,152 A | 11/1993 | Yang et al. |
| 5,277,181 A | 1/1994 | Mendelson et al. |
| 5,278,627 A | 1/1994 | Aoyagi et al. |
| 5,313,941 A | 5/1994 | Braig et al. |
| 5,321,501 A | 6/1994 | Swanson et al. |
| 5,337,744 A | 8/1994 | Branigan |
| 5,341,805 A | 8/1994 | Stavridi et al. |
| 5,348,003 A | 9/1994 | Caro |
| 5,349,953 A | 9/1994 | McCarthy et al. |
| 5,361,758 A | 11/1994 | Hall et al. |
| D353,195 S | 12/1994 | Savage et al. |
| D353,196 S | 12/1994 | Savage et al. |
| 5,370,114 A | 12/1994 | Wong et al. |
| 5,376,336 A | 12/1994 | Lubbers et al. |
| 5,377,676 A | 1/1995 | Vari et al. |
| 5,379,238 A | 1/1995 | Stark |
| 5,383,452 A | 1/1995 | Buchert |
| 5,398,681 A | 3/1995 | Kupershmidt |
| D359,546 S | 6/1995 | Savage et al. |
| 5,431,170 A | 7/1995 | Mathews |
| 5,433,197 A | 7/1995 | Stark |
| 5,435,309 A | 7/1995 | Thomas et al. |
| D361,840 S | 8/1995 | Savage et al. |
| D362,063 S | 9/1995 | Savage et al. |
| 5,448,992 A | 9/1995 | Kupershmidt |
| 5,452,716 A | 9/1995 | Clift |
| 5,452,717 A | 9/1995 | Branigan et al. |
| D363,120 S | 10/1995 | Savage et al. |
| 5,456,252 A | 10/1995 | Vari et al. |
| 5,457,535 A | 10/1995 | Schmidtke et al. |
| 5,459,570 A | 10/1995 | Swanson et al. |
| 5,482,036 A | 1/1996 | Diab et al. |
| 5,490,505 A | 2/1996 | Diab et al. |
| 5,492,118 A | 2/1996 | Gratton et al. |
| 5,494,043 A | 2/1996 | O'Sullivan et al. |
| 5,501,226 A | 3/1996 | Petersen et al. |
| 5,533,511 A | 7/1996 | Kaspari et al. |
| 5,535,743 A | 7/1996 | Backhaus et al. |
| 5,549,114 A | 8/1996 | Petersen et al. |
| 5,551,422 A | 9/1996 | Simonsen et al. |
| 5,553,616 A | 9/1996 | Ham et al. |
| 5,561,275 A | 10/1996 | Savage et al. |
| 5,562,002 A | 10/1996 | Lalin |
| 5,582,168 A | 12/1996 | Samuels et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,710,630 A | 1/1998 | Essenpreis et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,795,295 A | 8/1998 | Hellmuth et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,036,919 A | 3/2000 | Thym et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,147,108 A | 11/2000 | Hauptman |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,294,062 B1 | 9/2001 | Buck, Jr. et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |

| | | |
|---|---|---|
| 6,397,091 B2 | 5/2002 | Diab et al. |
| 6,425,863 B1 | 7/2002 | Werner et al. |
| 6,430,525 B1 | 8/2002 | Weber et al. |
| 6,443,881 B1 | 9/2002 | Finger |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,216 B1 | 4/2003 | Wilsey et al. |
| 6,541,756 B2 | 4/2003 | Schulz et al. |
| 6,542,764 B1 | 4/2003 | Al-Ali et al. |
| 6,544,212 B2 | 4/2003 | Galley et al. |
| 6,556,853 B1 | 4/2003 | Cabib et al. |
| 6,572,566 B2 | 6/2003 | Effenhauser |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,707,554 B1 | 3/2004 | Miltner et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,073 B1 | 4/2004 | Motamedi et al. |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,780,651 B2 | 8/2004 | Douglas et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,836,337 B2 | 12/2004 | Cornsweet |
| 6,837,337 B2 | 1/2005 | Thomas et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,734 B2 | 12/2007 | Dogariu |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B2 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |

| | | | |
|---|---|---|---|
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,526,328 | B2 | 4/2009 | Diab et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,596,398 | B2 | 9/2009 | Al-Ali et al. |
| 7,618,375 | B2 | 11/2009 | Flaherty |
| D606,659 | S | 12/2009 | Kiani et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| RE41,317 | E | 5/2010 | Parker |
| 7,729,733 | B2 | 6/2010 | Al-Ali et al. |
| 2002/0016533 | A1 | 2/2002 | Marchitto et al. |
| 2004/0260158 | A1* | 12/2004 | Hogan ................. 600/316 |
| 2005/0059868 | A1 | 3/2005 | Schurman |
| 2005/0070771 | A1 | 3/2005 | Rule et al. |
| 2005/0101846 | A1* | 5/2005 | Fine et al. ............. 600/316 |
| 2005/0105097 | A1* | 5/2005 | Fang-Yen et al. ....... 356/497 |
| 2005/0186648 | A1 | 8/2005 | Schurman |
| 2005/0254061 | A1* | 11/2005 | Alphonse ............. 356/479 |
| 2006/0063988 | A1 | 3/2006 | Schurman |
| 2006/0276696 | A1 | 12/2006 | Schurman |

FOREIGN PATENT DOCUMENTS

| | | |
|---|---|---|
| EP | 0160768 | 5/1989 |
| EP | 0127947 | 8/1990 |
| EP | 0280986 | 7/1992 |
| EP | 0317121 | 2/1994 |
| EP | 0589191 | 3/1997 |
| EP | 0603658 | 2/1999 |
| EP | 0631137 | 3/2002 |
| EP | 0670143 | 5/2003 |
| WO | WO 88/06726 | 9/1988 |
| WO | WO 89/10087 | 11/1989 |
| WO | WO 91/18548 | 12/1991 |
| WO | WO 92/10131 | 6/1992 |
| WO | WO 92/17765 | 10/1992 |
| WO | WO 93/00855 | 1/1993 |
| WO | WO 93/07801 | 4/1993 |
| WO | WO 93/09421 | 5/1993 |
| WO | WO 93/16629 | 9/1993 |
| WO | WO 94/04070 | 3/1994 |
| WO | WO 94/13193 | 6/1994 |
| WO | WO 95/32416 | 11/1995 |
| WO | WO 02/65090 | 8/2002 |

OTHER PUBLICATIONS

Arnold, V.W. et al., "Fourier Transformation Infrared Spectrometry—A New (Old) Method of Detection in Forensic Chemistry and Criminal Investigation," Beitr Gerichtl Med. 47:123-47 (1989).

Bruulsema, J.T. et al., "Correlation Between Blood Glucose Concentration in Diabetics and Noninvasively Measured Tissue Optical Scattering Coefficient," Opt. Lett. 22(3):190-93 (1997).

Burritt, M.F., "Current Analytical Approaches to Measuring Blood Analytes," Clin. Chem. 36(8 pt.2):1562-66 (1990).

Chira, I.S. et al., "Light Scattering by Blood Components After Supplying Glucose," Biomed. Tech. 35(5):102-06 (1990).

Christison, G.B. et al., "Laser Photoacoustic Determination of Physiological Glucose Concentrations in Human Whole Blood," Med. Biol. Eng. Comput. 31(3):284-90 (1993).

Cote, G.L. et al., "Noninvasive Optical Polarimetric Glucose Sensing Using a True Phase Measurement Technique," IEEE Trans. Biomed. Eng. 39(7):752-56 (1992).

Dyer, D.G. et al., "Accumulation of Maillard Reaction Products in Skin Collagen in Diabetes and Aging," J. Clin. Invest. 91:2463-69 (1993).

Esenaliev, R.O. et al., "Noninvasive Monitoring of Glucose Concentration with Optical Coherence Tomography," Optics Lett. 26(13):992-94 (2001).

Faber, D.J. et al., "Light Absorption of (oxy-)Hemoglobin Assessed by Spectroscopic Optical Coherence Tomography," Optics Lett. 28(16):1436-38 (2003).

Fercher, A. et al., "In Vivo Optical Coherence Tomography," Amer. J. Opthalmol. 116(1):113-14 (1993).

Flock, S.T. et al., "Total Attentuation Coefficients and Scattering Phase Functions of Tissues and Phantom Materials at 633 nm," Med. Phys. 14(5):835-41 (1987).

Fogt, E.J., "Continuous Ex Vivo and In Vivo Monitoring with Chemical Sensors," Clin. Chem. 36(8 pt.2):1573-80 (1990).

Frank, K.H. et al., "Measurements of Angular Distributions of Rayleigh and Mie Scattering Events in Biological Models," Phys. Med. Biol. 34(8):1901-16 (1989).

Gabriely, I. et al., "Transcutaneous Glucose Measurement Using Near-Infrared Spectroscopy During Hypoglycemia," Diabetes Care 22(12):2026-32 (1999).

Galanzha, E.I. et al., "Skin Backreflectance and Microvascular System Functioning at the Action of Osmotic Agents," J. Phys. D. Appl. Phys. 36:1739-46 (2003).

Gilbert, J.W. et al., "A Cerebrospinal Fluid Glucose Biosensor for Diabetes Mellitus," ASAIO J. 38(2):82-87 (1992).

Goetz, M.J. et al., "Application of a Multivariate Technique to Raman Spectra for Quantification of Body Chemicals," IEEE Trans. Biomed. Eng. 42:728-31 (1995).

Goodman, J.W., Some Fundamental Properties of Speckle, J. Optical Soc. of America 66(11):1145-50 (1976).

Gough, D.A., "The Composition and Optical Rotary Dispersion of Bovine Aqueous Humor," Diabetes Care 5(3):266-70 (1982).

Gunby, P., "Laser-Implant Contact Lens Could be Glucose Monitor," JAMA 243(4):317 (1980).

Huang, D. et al., "Optical Coherence Tomograph," Science 254:1178-81 (1991).

Huang, Y.L. et al., "On-Line Determination of Glucose Concentration Throughout Animal Cell Cultures Based on Chemiluminescent Detection of Hydrogen Peroxide Coupled with Flow-Injection Analysis," J. Biotechnol. 18(1-2):161-72 (1991).

Kaiser, N., "Laser Absorption Spectroscopy with an ATR Prism—Noninvasive in Vivo Determination of Glucose," Horm. Metab. Res. Suppl. 8:30-33 (1979).

Kajiwara, K. et al., "Spectroscopic Quantitative Analysis of Blood Glucose by Fourier Transform Infrared Spectroscopy with an Attenuated Total Reflection Prism," Med. Prog. Technol. 18(3):181-89 (1992).

Khalil, O.S., "Spectroscopic and Clinical Aspects of Noninvasive Glucose Measurements," Clin. Chem. 45(2):165-77 (1999).

Kholodnykh, A.I. et al., "Precision of Measurement of Tissue Optical Properties with Optical Coherence Tomography," Appl. Optics 42(16):3027-37 (2003).

King, T.W. et al., "Multispectral Polarimetric Glucose Detection Using a Single Pockels Cell," Optical Engineering 33(8):2746-53 (1994).

Kohl, M. et al., "The Influence of Glucose Concentration Upon the Transport of Light in Tissue-Simulating Phantoms," Phys. Med. Biol. 40:1267-87 (1995).

Kohl, M. et al., "Influence of Glucose Concentration on Light Scattering in Tissue-Simulating Phantoms," Optics Letters 19(24):2170-72 (1994).

Kruse-Jarres, J.D., "Physicochemical Determinations of Glucose in Vivo," J. Clin. Chem. Clin. Biochem. 26(4):201-08 (1988).

Larin, K.V. et al., "Optoacoustic Signal Profiles for Monitoring Glucose Concentration in Turbid Media," SPIE Proc. 3726:576-83 (1988).

Larin, K.V. et al., "Noninvasive Blood Glucose Monitoring With Optical Coherence Tomography," Diabetes Care 25(12):2263-67 (2002).

Larin, K.V. et al., "Specificity of Noninvasive Blood Glucose Sensing Using Optical Coherence Tomography Technique: A Pilot Study," Physics in Med. & Biol. 48:1371-90 (2003).

Larin, K.V. et al., "Phase-Sensitive Optical Low-Coherence Reflectometry for the Detection of Analyte Concentrations," Appl. Optics 43(17):3408-14 (2004).

Mackenzie, H.A. et al., "Advances in Photoacoustic Noninvasive Glucose Testing," Clin. Chem. 45(9):1587-95 (1999).

Maier, J.S. et al., "Possible Correlation Between Blood Glucose Concentration and the Reduced Scattering Coefficient of Tissues in the Near Infrared," Optics Lett. 19(24):2062-64 (1994).

March, W. et al., "Optical Monitor of Glucose," Trans. Am. Soc. Artif. Intern. Organs 25:28-31 (1979).

March, W.F. et al., "Noninvasive Glucose Monitoring of the Aqueous Humor of the Eye: Part II. Animal Studies and the Scleral Lens," Diabetes Care 5(3):259-65 (1982).

Mendelson, Y. et al., "Blood Glucose Measurement by Multiple Attenuated Total Reflection and Infrared Absorption Spectroscopy," IEEE Trans. Biomed. Eng. 37(5):458-65 (1990).

Moreno-Bondi, M.C. et al., "Oxygen Optrode for Use in a Fiber-Optic Glucose Biosensor," Anal. Chem. 62(21):2377-80 (1990).

Muller, A., "In Vivo Measurement of Glucose Concentration with Lasers," Horm. Metab. Res. Suppl. 8:33-35 (1979).

Narayanaswamy, R., "Current Developments in Optical Biochemical Sensors," Biosens. Bioelectron. 6(6):467-75 (1991).

Pan, S. et al., "Near-Infrared Spectroscopic Measurement of Physiological Glucose Levels in Variable Matrices of Protein and Triglycerides," Anal. Chem. 68:1124-35 (1996).

Peterson, J.I. et al., "A Miniature Fiberoptic pH Sensor Potentially Suitable for Glucose Measurements," Diabetes Care 5(3)272-74 (1982).

Quan, K.M. et al., "Glucose Determination by a Pulsed Photoacoustic Technique—An Experimental Study Using a Gelatin-Based Tissue Phantom," Phys. Med. Biol. 38(12): 1911-22 (1993).

Rabinovitch, B. et al., "Noninvasive Glucose Monitoring of the Aqueous Humor of the Eye: Part I. Measurement of Very Small Optical Rotations," Diabetes Care 5(3):254-58 (1982).

Robinson, M.R. et al., "Noninvasive Glucose Monitoring in Diabetic Patients: A Preliminary Evaluation," Clin. Chem. 38(9):1618-22 (1992).

Robinson, R.J. et al., "Glucose-Sensitive Membrane and Infrared Absorption Spectroscopy for Potential Use as an Implantable Glucose Sensor," ASAIO J. 38(3):M458-62 (1992).

Rusch, T.L. et al., "Signal Processing Methods for Pulse Oximetry," Comput. Biol. Med. 26(2):143-59 (1996).

Schmitt, J.M. et al., "Measurement of Optical Properties of Biological Tissues by Low-Coherence Reflectometry," Appl. Optics 32(30):6032-42 (1993).

Schmitt, J.M. et al., "Optical Coherence Tomography (OCT): A Review," IEEE J. Selected Topics in Quantum Electronics 5(4):1205-15 (1999).

Schmitt, J.M. et al., "Speckle in Optical Coherence Tomography," J. Biomed. Optics 4(1):95-105 (1999).

Sevick, E.M. et al., "Near-Infrared Optical Imaging of Tissue Phantoms with Measurement in the Change of Optical Path Lengths," Adv. Exp. Med. Biol. 345:815-23 (1994).

Sodickson, L.A. et al., "Kromoscopic Analysis: A Possible Alternative to Spectroscopic Analysis for Noninvasive Measurement of Analytes in Vivo," Clin. Chem. 40(9):1838-44 (1994).

Star, W.M. et al., "Light Dosimetry: Status and Prospects," J. Photochem. Photobiol. 1(2):149-67 (1987).

Stoddart, S. et al., "Pulse Oximetry: What it is and How to Use it, " J. Neonatal Nursing 10:12-14 (1997).

Takai, N. et al., "Studies of the Development of Optical Fiber Sensors for Biochemical Analysis," Artif. Organs 15(2):86-89 (1991).

Tunchin, V.V. et al., "Light Propagation in Tissues with Controlled Optical Properties," J. Biomed. Opt. 2(4):401-17 (1997).

Wang, L. et al., "Speckle Reduction in Laser Projection Systems by Diffractive Optical Elements," Appl. Optics 37(10):1770-75 (1998).

Welch, A.J. et al., Practical Models for Light Distribution in Laser-Irradiated Tissue, Lasers Surg. Med. 6(6):488-93 (1987).

Wicksted, J.P. et al., "Monitoring of Aqueous Humor Metabolites Using Raman Spectroscopy," SPIE Proc. 2135:264-74 (1994).

Zeller, H. et al., "Blood Glucose Measurement by Infrared Spectroscopy," J. Artif. Organs 12(2):129-35 (1989).

* cited by examiner

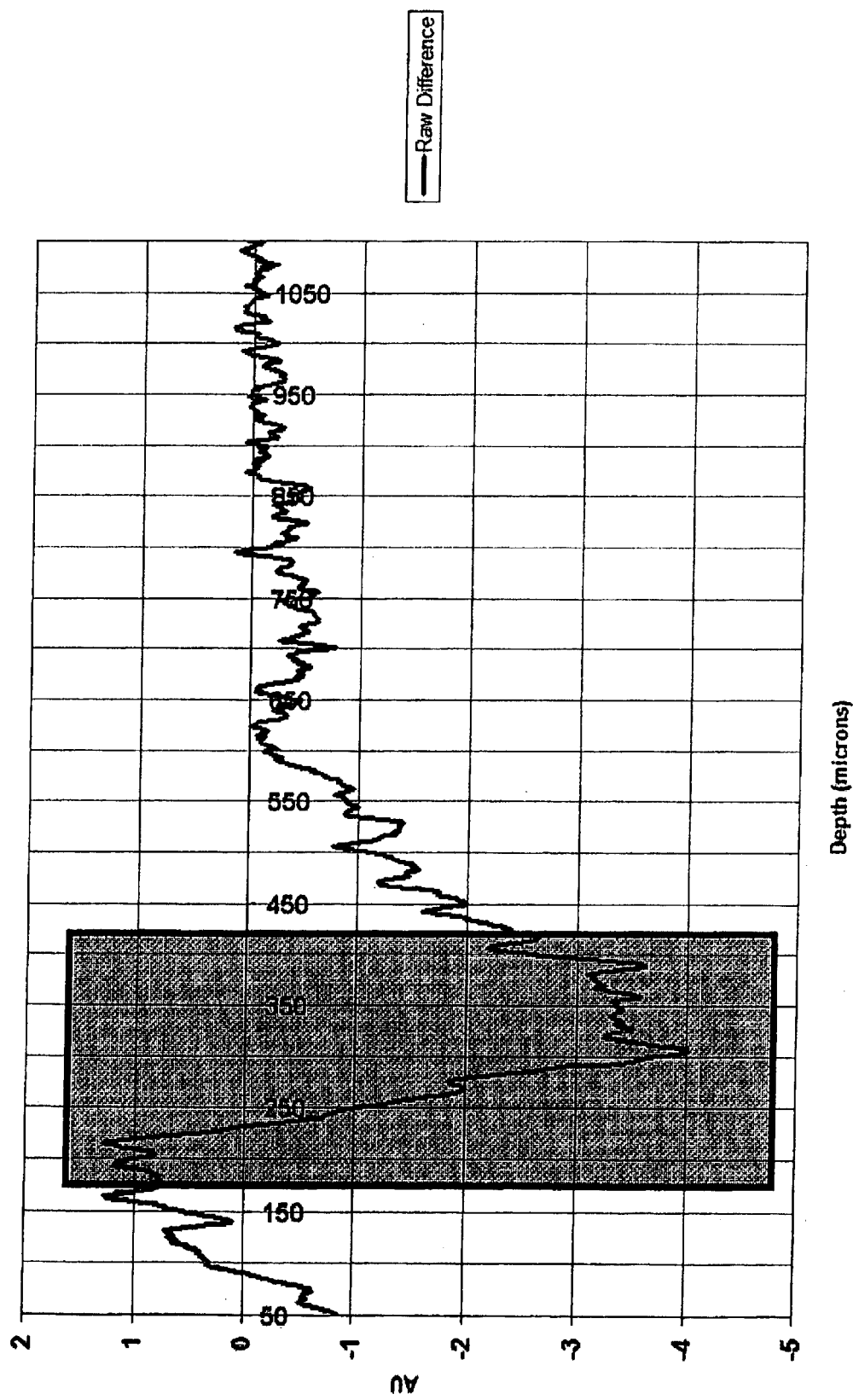

Vector Glucose Grid

| Interval \ Offset | 100 | 125 | 150 | 175 | 200 | 225 | 250 | 275 |
|---|---|---|---|---|---|---|---|---|
| 50 | N/A | N/A | N/A | N/A | -12.5579 | -10.3634 | -10.1949 | -9.19149 |
| 75 | N/A | N/A | N/A | -9.01149 | -11.5238 | -10.0762 | -9.18383 | -5.42298 |
| 100 | N/A | N/A | -5.48043 | -10.1145 | -10.9034 | -9.67404 | -7.14255 | N/A |
| 125 | N/A | -5.53021 | -8.09234 | -10.1681 | -10.2868 | -8.2417 | -5.71021 | N/A |
| 150 | N/A | -7.06979 | -8.79702 | -9.95745 | -9.15702 | -7.0966 | -4.80255 | N/A |
| 175 | N/A | -7.7783 | -9.08809 | -9.10723 | -8.16128 | -6.37277 | N/A | N/A |
| 200 | -5.65277 | -7.61745 | -8.57872 | -8.31447 | -7.4183 | -5.12426 | N/A | N/A |
| 225 | -6.61021 | -7.28043 | -8.0234 | -7.75915 | -6.4034 | N/A | N/A | N/A |
| 250 | -6.73277 | -6.96638 | -7.56766 | -6.84383 | -5.1434 | N/A | N/A | N/A |
| 275 | -6.58723 | -6.41489 | -6.81702 | -5.76383 | N/A | N/A | N/A | N/A |
| 300 | -6.43021 | -5.65277 | -5.94766 | -4.79106 | N/A | N/A | N/A | N/A |
| 325 | -5.98596 | -4.89064 | -5.05532 | N/A | N/A | N/A | N/A | N/A |
| 350 | -5.36553 | N/A | N/A | N/A | N/A | N/A | N/A | N/A |
| 375 | -4.7566 | N/A | N/A | N/A | N/A | N/A | N/A | N/A |
| 400 | N/A | N/A | N/A | N/A | N/A | N/A | N/A | N/A |
| 425 | N/A | N/A | N/A | N/A | N/A | N/A | N/A | N/A |
| 450 | N/A | N/A | N/A | N/A | N/A | N/A | N/A | N/A |
| 475 | N/A | N/A | N/A | N/A | N/A | N/A | N/A | N/A |
| 500 | N/A | N/A | N/A | N/A | N/A | N/A | N/A | N/A |

Figure 5

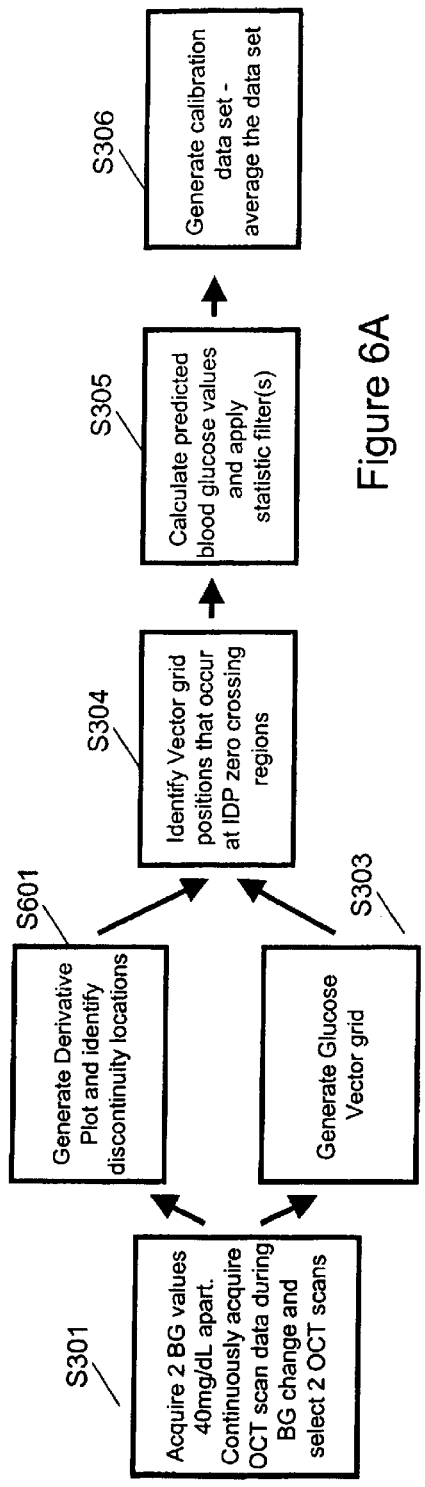
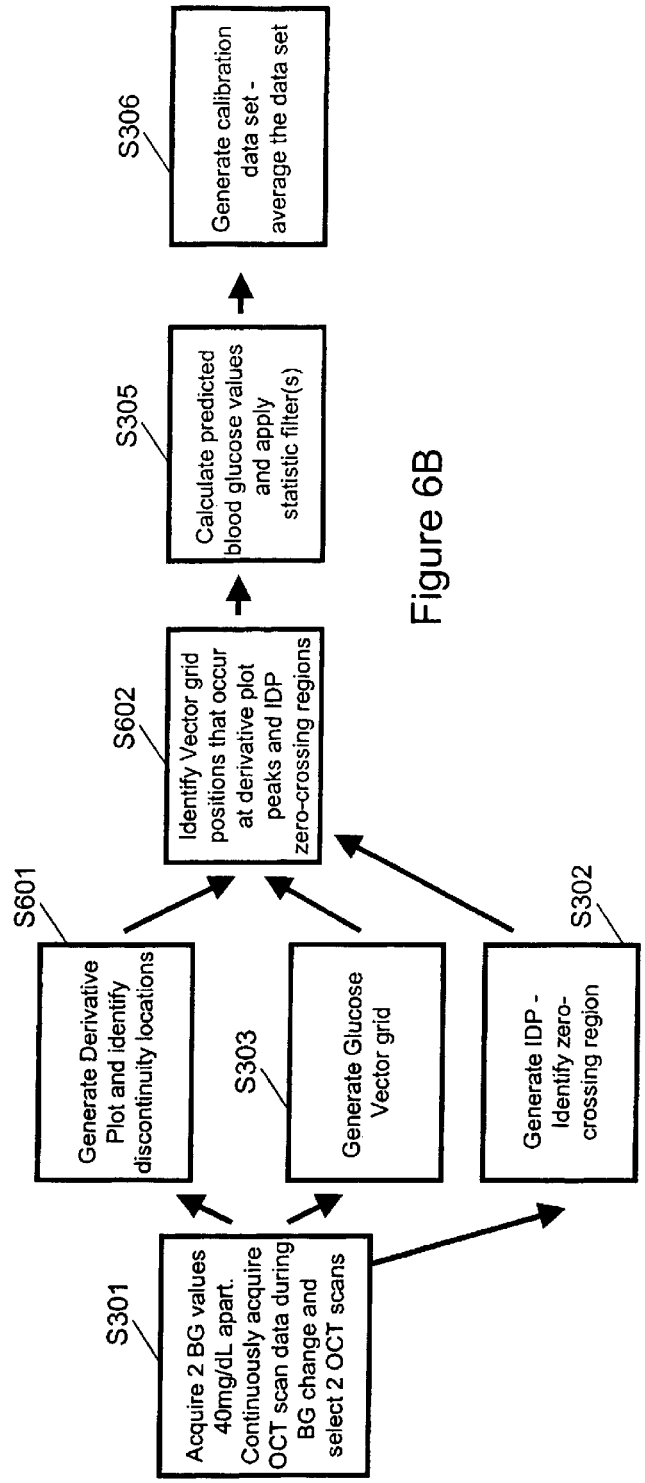
Figure 6A
Figure 6B

ND CALIBRATION OF AN OCT-BASED BLOOD
METHOD FOR DATA REDUCTION AND CALIBRATION OF AN OCT-BASED BLOOD GLUCOSE MONITOR

CROSS REFERENCE TO RELATED APPLICATIONS

This application claims priority benefit of U.S. Provisional Applications Ser. Nos. 60/671,007 filed Apr. 13, 2005 and 60/671,285 filed Apr. 14, 2005, and of U.S. application Ser. No. 10/916,236 filed on Aug. 11, 2004, now U.S. Pat. No. 7,254,429, of which this application is a continuation-in-part, each of which is incorporated herein by reference in its entirety.

FIELD OF THE INVENTION

The present invention relates to a method for estimating blood glucose levels using a noninvasive optical coherence tomography- (OCT-) based blood glucose monitor.

BACKGROUND OF THE INVENTION

Monitoring of blood glucose (i.e., blood sugar) levels has long been critical to the treatment of diabetes in humans. Current blood glucose monitors involve a chemical reaction between blood serum and a test strip, requiring an invasive extraction of blood via a lancet or pinprick to the finger. Small handheld monitors have been developed to enable a patient to perform this procedure anywhere, at any time. The inconvenience associated with this procedure—specifically, the blood extraction and the need for test strips-has led to a low level of compliance by diabetic patients. Such low compliance can lead to diabetic complications. Thus, a non-invasive method for monitoring blood glucose is needed.

Studies have shown that optical methods can be used to detect small changes in light scattering from biological tissue related to changes in levels of blood sugar. Although highly complex, a first order approximation of the relationship of the intensity of monochromatic light reflected by biological tissue can be described by the following simplified equation:

$$I_R = I_O \exp[-(\mu_a + \mu_s)L],$$

where $I_R$ is the intensity of light reflected from the skin, $I_O$ is the intensity of the light illuminating the skin, $\mu_a$ is the absorption coefficient of the skin at the specific wavelength of the light, $\mu_s$ is the scattering coefficient of the skin at the specific wavelength of the light, and L is the total path traversed by the light. From this relationship it can be seen that the intensity of the light reflected from the skin decays exponentially as either the absorption or the scattering by the tissue increases.

It is well established that there is a difference in the index of refraction between blood serum/interstitial fluid (IF) and cell membranes (such as, membranes of blood cells and skin cells). (See, R. C. Weast, ed., CRC Handbook of Chemistry and Physics, 70th ed. (CRC Cleveland, Ohio 1989.)) This difference can produce characteristic scattering of transmitted light. Glucose, in its varying forms, is a major constituent of blood and IF. The variation in glucose levels in either blood or IF changes its refractive index and thus, the characteristic scattering from blood-perfused tissue. In the near-infrared (NIR) wavelength range (i.e., wherein the center wavelength of the optical source is about 770 nm to about 1400 nm), blood glucose changes the scattering coefficient of the light, $\mu_s$, more than it changes the absorption coefficient of the light, $\mu_a$. Thus, the optical scattering of the blood/IF and cell combination varies as the blood glucose level changes. Accordingly, there is the potential for non-invasive measurement of blood glucose levels.

Non-invasive optical techniques being explored for blood glucose applications include polarimetry, Raman spectroscopy, near-infrared absorption, scattering spectroscopy, photoacoustics, and optoacoustics. Despite significant efforts, these techniques have shortcomings, such as low sensitivity, low accuracy (less than that of current invasive home monitors), and insufficient specificity of glucose level measurement within the relevant physiological range of about 4 mM/L to about 30 mM/L or about 72 to about 540 (mg/dL). Accordingly, there is a need for a method to conveniently, accurately, and non-invasively monitor glucose levels in blood.

Optical coherence tomography, or OCT, is an optical imaging technique that uses light waves to produce high-resolution imagery of biological tissue. OCT produces images by interferometrically scanning, in depth, a linear succession of spots and measuring absorption and/or scattering at different depths at each successive spot. The data then is processed to present an image of the linear cross section. Although it has been proposed that OCT might be useful in measuring blood glucose, a difficulty associated with this technique is identifying which portion(s) of a patient's OCT signal closely correlate(s) with a patient's blood glucose level and then calibrating a change of the identified OCT signal portion(s) to a change in the patient's blood glucose level, so that the changes in a patient's OCT signal may be used to predict changes in the patient's blood glucose level. However, a method now has been found that maximizes the correlation between the OCT signal from a patient's skin and the patient's blood glucose levels, thereby providing a means for calibrating a device, such as an OCT-based blood glucose monitor, for non-invasive, accurate and sensitive prediction of the patient's blood glucose level. The present invention is directed to this method and other related unmet needs.

SUMMARY OF INVENTION

The present invention provides a noninvasive method of determining estimated blood glucose levels in a biological tissue of a subject using an optical coherence tomography-based blood glucose monitor comprising a sensor and at least one algorithm, the method comprising the steps: (a) selecting a wavelength of light for which $\mu_a$, an absorption coefficient of the biological tissue, is small relative to $\mu_s$, a scattering efficient of the tissue for the selected wavelength of light; (b) continuously scanning a two-dimensional surface area of the biological tissue and interferometrically scanning the two-dimensional surface area of the biological tissue in a depth dimension with the light during a time period; (c) averaging the data obtained by interferometrically scanning the two-dimensional surface area of the biological tissue in a depth dimension with the light to generate a multitude of optical coherence tomography scan data lines in the time period, wherein the x-axis of each optical coherence tomography scan data line is depth and the y-axis of each optical coherence tomography scan data lines is intensity; (d) calibrating the optical coherence tomography-based sensor against at least two invasively obtained blood glucose measurements taken during the time period; and (e) allowing the calibrated optical coherence tomography-based sensor and the at least one algorithm to determine an estimated blood glucose level in the biological tissue. In one embodiment, the wavelength of light in step (a) of the method is within the range of about 770 nm to about 1400 nm. In another embodiment, calibrating step (c) of the method further comprising the steps (i) generating a calibration set of estimated blood glucose values; and (ii) applying the calibration set to calibrate the optical coherence tomography-based blood glucose monitor. In another embodiment, in step (c) of the method, the optical coherence tomography-based blood glucose monitor is calibrated by a programmable computer. In another embodiment, substep (i) of calibrating step (c) of the method further comprises the steps: (a) selecting at least two invasively obtained blood glucose measurements obtained over a time period, wherein the at least two measurements are spaced apart by a concentration value of at least about 40 mg/dL; (b) selecting two optical coherence tomography scan data lines, each scan data line having been obtained on or about the time period; (c) computing intensity differences between the two selected optical coherence tomography scan data lines by subtracting a first baseline scan data line (n) from a second, subsequent optical coherence tomography scan data line (n+1) at every point along the two selected optical coherence tomography scan data lines to generate an intensity difference plot; and (d) using the intensity difference plot to determine a multitude of offsets and a multitude of intervals to construct a glucose vector grid comprising a multitude of offset, interval pairs. In another embodiment, the glucose vector grid in step (d) of the method further comprises a percentage change value corresponding to each offset, interval pair. In another embodiment, wherein the method to obtain the percentage change value for each offset, interval pair comprises the steps: (i) calculating a first slope value for a line segment from the first baseline scan data line and a second slope value for a line segment from the second, subsequent optical coherence tomography scan data line for each potential offset and interval pair; and (ii)calculating the difference between the first slope value and the second slope value for each potential offset and interval pair to obtain a percentage change value for each potential offset and interval pair.

In another embodiment, the method further comprises the steps: (e) determining a scattering coefficient proportional to a slope of each optical coherence tomography scan data line for each potential offset, interval pair; (f)creating a calibration curve correlating scattering coefficients and blood glucose values by performing a regression analysis, wherein each x-value comprises a scattering coefficient corresponding to the scattering coefficient of an invasively obtained blood glucose measurement and each y-value comprises the blood glucose value measured from each invasively obtained blood glucose measurement; (g) calculating a set of estimated blood glucose values from the scattering coefficients for each potential offset, interval pair; (h) refining the set of estimated blood glucose values; (i) averaging the sets of estimated blood glucose values for each point in time to generate the calibration set; and (j) applying the calibrated sensor comprising the calibration set and selected offset, interval pairs to all subsequent optical coherence tomography scans. In another embodiment, step (d) of the method further comprises the steps (i) identifying at least one data point in the intensity difference plot where intensity is 0, at least one data point having a maximum intensity surrounding the at least one data point where intensity is 0, and at least one data point having a minimum intensity surrounding the at least one data point where intensity is 0; and (ii) identifying a potential offset range, wherein a first boundary of the potential offset range is the at least one data point having a maximum intensity surrounding the at least one data point where intensity is 0 and a second boundary of the potential offset range is the at least one data point having a minimum intensity surrounding the at least one data point where intensity is 0. In another embodiment, wherein the time period includes a blood glucose altering event. In another embodiment, the blood glucose altering event is administering insulin. In another embodiment, the blood glucose altering event is eating a meal. In another embodiment, the blood glucose altering event is drinking a beverage containing sugar.

In another embodiment, refining step (h) of the method further comprises the step applying at least one statistical filter. In another embodiment, the statistical filter refines a set of average estimated blood glucose values from each potential offset, interval pair by ignoring sets of estimated blood glucose values that are outside one standard deviation of the set of average estimated blood glucose values at any point in time. In another embodiment, the statistical filter refines a set of median estimated blood glucose values by ignoring sets of estimated blood glucose values that are outside one standard deviation of the set of median estimated blood glucose values at any point in time. In another embodiment, prior to generating the calibration set of estimated blood glucose values, the at least one statistical filter eliminates negative estimated blood glucose values. In another embodiment, prior to generating the calibration set of estimated blood glucose values, the at least one statistical filter eliminates estimated blood glucose values of less than about 10 mg/dL. In another embodiment, prior to generating the calibration set of estimated blood glucose values, the at least one statistical filter eliminates high estimated blood glucose values. In another embodiment, prior to generating the calibration set of estimated blood glucose values, the at least one statistical filter operates in accordance with equation (1). In another embodiment, prior to generating a calibration set of estimated blood glucose values, the at least one statistical filter operates in accordance with equation (2).

In another embodiment, the method further comprising the steps (e) enhancing at least one discontinuity in each selected optical coherence tomography scan data line; and (f) using the at least one discontinuity to generate the potential offsets of the multitude of offset, interval pairs. In another embodiment, step (e) of the method further comprising the step: generating a second derivative plot of the optical coherence tomography scan data line. In another embodiment, the method further comprises the step of identifying potential offsets by using the at least one discontinuity. In another embodiment, the at least one discontinuity indicates potential offsets that correlate closely to locations of a tissue interface transition. In another embodiment, the tissue interface transition is a blood vessel. In another embodiment, the discontinuity corresponds to changes in blood glucose levels.

In another embodiment, calibration step (c) of the method further comprises the steps: (i) using a Pearson's plot to calibrate the optical coherence tomography-based sensor against at least two invasively obtained blood glucose measurements taken during the time period; and (ii) using Pearson's correlation to maximize the correlation between data received from the optical coherence tomography-based glucose monitor and the invasively obtained glucose measurements. In another embodiment, the Pearson's plot in step (i) requires at least seven blood glucose measurements invasively obtained over the time period.

The present invention further provides a noninvasive method of providing an estimated blood glucose level to a subject in need thereof, the method comprising the steps of: (a)identifying a subject in need thereof, (b)calibrating an optical coherence tomography blood glucose monitor comprising a sensor and at least one algorithm against at least two invasively obtained blood glucose measurements taken during a time period; (c) identifying a biological tissue of the subject to be scanned by the calibrated optical coherence tomography blood glucose monitor; (d)continuously scanning a two-dimensional surface area of the biological tissue and interferometrically scanning the two-dimensional surface area of the biological tissue in a depth dimension with the light during the time period; (e) averaging the data obtained by interferometrically scanning the two-dimensional surface area of the biological tissue in a depth dimension with the light to generate a multitude of optical coherence tomography scan data lines in the time period, wherein the x-axis of each optical coherence tomography scan data line is depth and the y-axis of each optical coherence tomography scan data lines is intensity; and (f) allowing the at least one algorithm to determining the estimated blood glucose level in the biological tissue from the multitude of optical coherence tomography scan data lines. In one embodiment, calibrating step (b) of the method further comprises the steps (i)generating a calibration set of estimated blood glucose values; and (ii)applying the calibration set to calibrate the optical coherence tomography-based blood glucose monitor. In another embodiment, in step (b) of the method, the optical coherence tomography-based blood glucose monitor is calibrated by a programmable computer. In another embodiment, In another embodiment, substep (i) of calibrating step (c) of the method further comprises the steps: (a) selecting at least two invasively obtained blood glucose measurements obtained over a time period, wherein the at least two measurements are spaced apart by a concentration value of at least about 40 mg/dL; (b) selecting two optical coherence tomography scan data lines, each scan data line having been obtained on or about the time period; (c) computing intensity differences between the two selected optical coherence tomography scan data lines by subtracting a first baseline scan data line (n) from a second, subsequent optical coherence tomography scan data line (n+1) at every point along the two selected optical coherence tomography scan data lines to generate an intensity difference plot; and (d) using the intensity difference plot to determine a multitude of offsets and a multitude of intervals to construct a glucose vector grid comprising a multitude of offset, interval pairs. In another embodiment, the glucose vector grid in step (d) of the method further comprises a percentage change value corresponding to each offset, interval pair. In another embodiment, wherein the method to obtain the percentage change value for each offset, interval pair comprises the steps: (i) calculating a first slope value for a line segment from the first baseline scan data line and a second slope value for a line segment from the second, subsequent optical coherence tomography scan data line for each potential offset and interval pair; and (ii) calculating the difference between the first slope value and the second slope value for each potential offset and interval pair to obtain a percentage change value for each potential offset and interval pair.

In another embodiment, the method further comprises the steps: (e) determining a scattering coefficient proportional to a slope of each optical coherence tomography scan data line for each potential offset, interval pair; (f) creating a calibration curve correlating scattering coefficients and blood glucose values by performing a regression analysis, wherein each x-value comprises a scattering coefficient corresponding to the scattering coefficient of an invasively obtained blood glucose measurement and each y-value comprises the blood glucose value measured from each invasively obtained blood glucose measurement; (g) calculating a set of estimated blood glucose values from the scattering coefficients for each potential offset, interval pair; (h) refining the set of estimated blood glucose values; (i) averaging the sets of estimated blood glucose values for each point in time to generate the calibration set; and (j) applying the calibrated sensor comprising the calibration set and selected offset, interval pairs to all subsequent optical coherence tomography scans. In another embodiment, step (d) of the method further comprises the steps (i) identifying at least one data point in the intensity difference plot where intensity is 0, at least one data point having a maximum intensity surrounding the at least one data point where intensity is 0, and at least one data point having a minimum intensity surrounding the at least one data point where intensity is 0; and (ii) identifying a potential offset range, wherein a first boundary of the potential offset range is the at least one data point having a maximum intensity surrounding the at least one data point where intensity is 0 and a second boundary of the potential offset range is the at least one data point having a minimum intensity surrounding the at least one data point where intensity is 0. In another embodiment, wherein the time period includes a blood glucose altering event. In another embodiment, the blood glucose altering event is administering insulin. In another embodiment, the blood glucose altering event is eating a meal. In another embodiment, the blood glucose altering event is drinking a beverage containing sugar.

In another embodiment, refining step (h) of the method further comprises the step applying at least one statistical filter. In another embodiment, the statistical filter refines a set of average estimated blood glucose values from each potential offset, interval pair by ignoring sets of estimated blood glucose values that are outside one standard deviation of the set of average estimated blood glucose values at any point in time. In another embodiment, the statistical filter refines a set of median estimated blood glucose values by ignoring sets of estimated blood glucose values that are outside one standard deviation of the set of median estimated blood glucose values at any point in time. In another embodiment, prior to generating the calibration set of estimated blood glucose values, the at least one statistical filter eliminates negative estimated blood glucose values. In another embodiment, prior to generating the calibration set of estimated blood glucose values, the at least one statistical filter eliminates estimated blood glucose values of less than about 10 mg/dL. In another embodiment, prior to generating the calibration set of estimated blood glucose values, the at least one statistical filter eliminates high estimated blood glucose values. In another embodiment, prior to generating the calibration set of estimated blood glucose values, the at least one statistical filter operates in accordance with equation (1). In another embodiment, prior to generating a calibration set of estimated blood glucose values, the at least one statistical filter operates in accordance with equation (2).

In another embodiment, the method further comprising the steps (e) enhancing at least one discontinuity in each selected optical coherence tomography scan data line; and (f) using the at least one discontinuity to generate the potential offsets of the multitude of offset, interval pairs. In another embodiment, step (e) of the method further comprising the step: generating a second derivative plot of the optical coherence tomography scan data line. In another embodiment, the method further comprises the step of identifying potential offsets by using the at least one discontinuity. In another embodiment, the at least one discontinuity indicates potential offsets that correlate closely to locations of a tissue interface transition. In another embodiment, the tissue interface transition is a blood vessel. In another embodiment, the discontinuity corresponds to changes in blood glucose levels.

In another embodiment, calibration step (c) of the method further comprises the steps: (i) using a Pearson's plot to calibrate the optical coherence tomography-based sensor against at least two invasively obtained blood glucose measurements taken during the time period; and (ii) using Pearson's correlation to maximize the correlation between data received from the optical coherence tomography-based glucose monitor and the invasively obtained glucose measurements. In another embodiment, the Pearson's plot in step (i) requires at least seven blood glucose measurements invasively obtained over the time period.

BRIEF DESCRIPTION OF THE DRAWINGS

The present invention will be more readily understood from the detailed description of the embodiments presented below considered in conjunction with the figures herein, of which:

FIG. 4. shows an example of an intensity difference plot, according to an embodiment of the present invention;

FIG. 5 shows an example of a glucose vector grid, according to an embodiment of the present invention;

FIGS. 6A and 6B illustrate process flows of a method for calibrating an OCT-based blood glucose monitor, according to embodiments of the present invention;

DETAILED DESCRIPTION OF THE INVENTION

Figure 1:
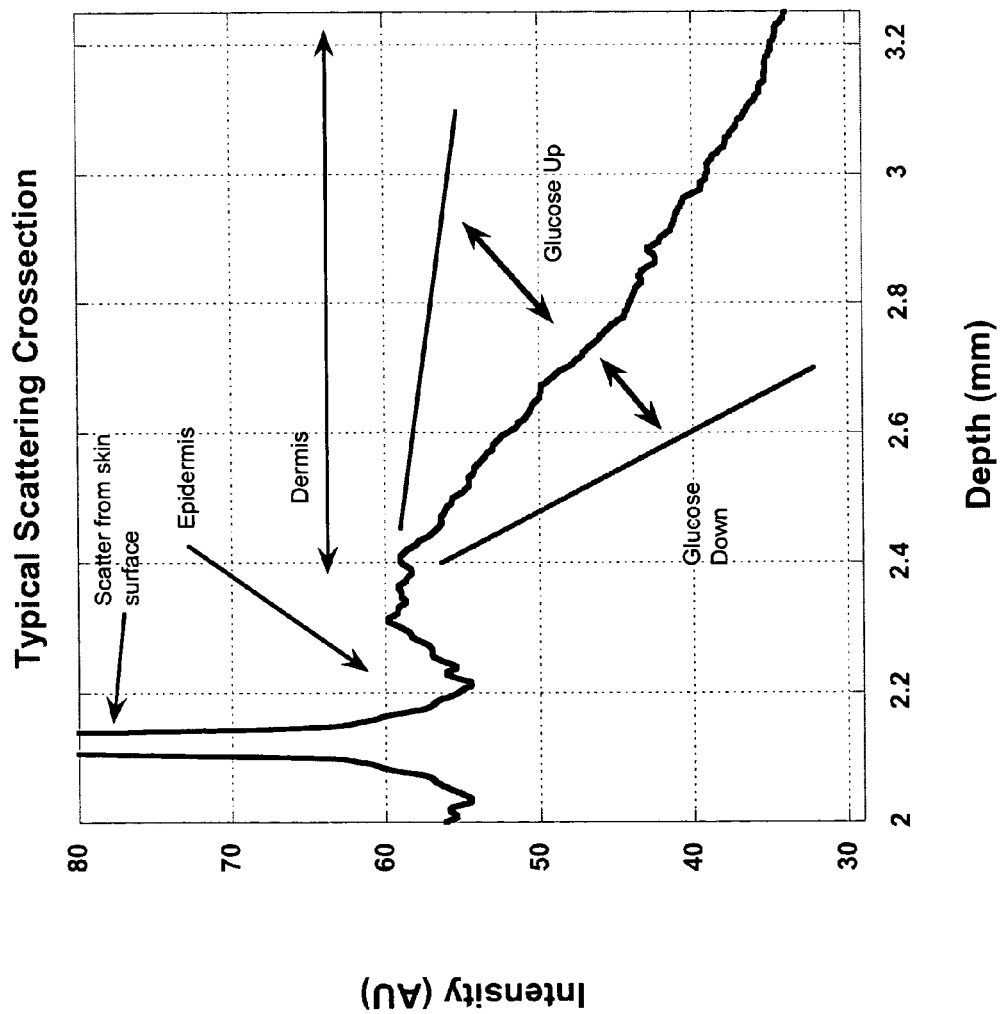
FIG. 1 is a graphical illustration of a typical scattering cross-section from a patch of human skin measured using an OCT-based blood glucose monitor.

When using an OCT-based blood glucose monitor to measure blood glucose levels or concentrations (also known as "serum glucose levels" or "sugar blood levels") in a biological tissue, the light provided by the OCT-based blood glucose monitor scatters throughout the biological tissue. The scattering of light changes in response to variations in blood glucose levels. Specifically, a scattering coefficient, $\mu_s$, which describes the attenuation of light due to the scattering of light by a biological tissue, rises and falls relative to variations in blood glucose levels. In accordance with the present invention, the blood glucose concentration or level within a biological tissue is monitored by providing a wavelength of light for which the attenuation is dominated by scattering effects and not absorption effects (i.e., such as absorption by water or hemoglobin), and continuously scanning the light over a two dimensional area of the biological tissue while, at the same time, interferometrically scanning the biological tissue in a depth dimension. By using a coordinate system defined so that the x-y axis forms the plane of the surface of the skin and the z axis is into the skin and parallel with the optical axis of the system, the term "depth dimension" refers to the dimension perpendicular to the surface of the skin and parallel with the optical axis of the system. The light reflected from the scanned biological tissue is collected and analyzed to determine the concentration of glucose in the biological tissue.

The present invention relates to a method for calibrating an OCT-based blood glucose monitor by maximizing the correlation between data produced by the OCT-based blood glucose monitor and measured blood glucose concentrations or levels. In one aspect of the present invention, an OCT scan data line can be utilized to maximize the correlation between the data received from the OCT-based blood glucose monitor and the measured blood glucose levels. As used herein, the term "scan data line" refers to the line formed from data obtained through the average of multiple OCT scans; the plot of this data is a plot of interferometric intensity versus depth. The scan data line, which is the average of multiple depth scans at different x-y locations over a given area, is an ensemble average of the scattering coefficient, as a function of depth, of the tissue volume being scanned.

In another aspect of the present invention, the Pearson Product Moment correlation method (Pearson's correlation) is utilized to maximize the correlation between the data received from the OCT-based blood glucose monitor and the measured blood glucose levels. Correlation results are used to calibrate the OCT-based blood glucose monitor, which then may be used to provide estimated blood glucose levels. Instead of determining blood glucose levels by current invasive methods, the blood glucose value obtained according to the present invention is estimated. Technically speaking then, a calibrated OCT glucose monitor according to the present invention provides a blood glucose level based on a calibrated prediction. The OCT-based blood glucose monitor thus may be used to provide estimated blood glucose levels to a user of the blood glucose monitor monitoring blood glucose levels, of for example, a diabetic subject, or of a subject with hyperglycemia (meaning high blood glucose levels, for example, $\geqq 126$ mg/dL), or of a subject with hypoglycemia (meaning low blood glucose levels, for example, $\leqq 70$ mg/dl).

According to an embodiment of the present invention, a method of correlating the OCT-based blood glucose monitor data with measured blood glucose levels includes a user taking multiple blood glucose measurements over a specified time period, preferably including a meal during that period, using a standard invasive method. The OCT-based blood glucose monitor uses a specific wavelength of light such that an absorption coefficient of light, $\mu_a$, of the biological tissue of the user is low relative to the scattering coefficient of light, $\mu_s$, within the biological tissue in order for variations in scattering of the light to be dominated by glucose-induced changes in scattering caused by the biological tissue. Multiple OCT scans are obtained at or around the same time period as when the blood glucose measurements are taken so that there is at least one OCT scan line per blood glucose measurement. The multiple OCT depth scans, which are averaged together to form the scan data line, should be accumulated within no more than about 5 min from the time the blood glucose value is determined. Data from each OCT scan is an averaged value of data obtained from a plurality of OCT scans performed automatically by the OCT-based blood glucose monitor in order to reduce any coherent noise or speckle produced by the OCT-based monitor itself. The data may be stored in the OCT-based blood glucose monitor or, alternatively, a programmable computer. OCT data provided by each averaged OCT scan may be plotted as interferometric intensity against the depth of the biological tissue, or against a set of depths of the biological tissue.

Due to the inherent heterogeneity of biological tissue and the uneven distribution of blood vessels in the dermis layer of biological tissue (i.e., the layer of skin beneath the epidermis), which is the preferred layer of skin for locating blood vessels, only specific segments or portions of an OCT scan-data line correlate to the actual blood glucose levels. Additionally, by knowing the specific wavelength of light-chosen, the dermis region of the biological tissue (e.g., of skin), which is where most blood vessels lie, may be determined easily from the data produced by the OCT-based blood glucose monitor.

There are two variables or parameters associated with fitting the obtained OCT data to the obtained blood glucose measurements in order to achieve the best correlation. These variables are an offset and an interval. The term "offset" as used herein refers to the depth of the OCT scan-data line/data curve) at which to begin correlating the OCT data to the blood glucose measurements, preferably in the dermis region of the biological tissue (e.g., of skin). This depth is referenced to the surface of the skin located at the skin/optical window interface. The term "interval" as used herein refers to a certain portion or segment of the OCT scan-data line that is measured from the offset. To determine the slope of any line segment, a linear least squares fit calculation generally is used to find the slope of the line. Alternatively, one can take the derivative of the line using any of a number of algorithms, one example of which is the finite difference, which is defined as subtraction of one adjacent point from another adjacent point. For each OCT scan-data line there are numerous potential combinations or pairs of offsets and intervals. The present invention reduces the number of potential pairs of offsets and intervals to pairs that are closely correlated to the measured blood glucose levels.

Blood glucose typically is represented either as a weight per unit volume by milligrams per deciliter (mg/dl) or as a molecular concentration in millimoles per liter (mM/L). A blood glucose level of 1 mM/L is equal to a level of 18 mg/dL. According to one aspect-of the present invention, the algorithm of the present invention selects two invasively measured blood glucose levels or blood glucose points that are spaced apart by a weight value of at least about 40 mg/dL, or about 2 mM/L. As soon as the algorithm sees two blood glucose levels more than about 40 mg/dL apart, it will begin the calibration process, which is depicted as box number 1 (S301) in FIG. 3*b*. The algorithm then selects two OCT scans taken at or around the same time as the selected blood glucose points. The selected OCT scans are used to reduce the data produced by the OCT-based blood glucose monitor to data that is closely correlated with the blood glucose measurements. Optionally, the algorithm may select several (averaged) OCT scans temporally located around the selected blood glucose points and average the data from the selected OCT scans in order to further reduce the speckle associated with the OCT-based blood glucose monitor.

The term "intensity difference plot ("IDP")" refers to a plot in which a baseline OCT scan (scan n) is subtracted from a subsequent OCT scan (scan (n+1)) to provide information on what regions of the scan line have changed from scan n to scan (n+1). According to the present invention, an intensity difference plot is generated by computing the difference in the intensity data of the two selected OCT scans. The intensity difference in the intensity data of the two selected OCT scans (the "intensity difference") is plotted against the depth of the tested biological tissue. With the present invention, it has now been observed that certain portions of an OCT scan-data line change dramatically as blood glucose levels vary, while certain other portions of an OCT scan-data line remain static as blood glucose levels vary. The intensity difference plot identifies the regions of the selected OCT scan-data lines that have the highest change in intensity. This change in intensity closely correlates (i.e., >95% confidence limit) to changes in blood glucose levels. Such dramatic changes in intensity also correlate closely (i.e., within a >95% confidence limit) to locations of a tissue transition interface, based on the depths of the tested biological tissue that corresponds to the changes in the intensity of the OCT signal. While one example of such a tissue transition interface is a blood vessel in the skin, structures other than blood vessels in the skin also could be changing with blood glucose levels. Blood vessels in the skin generally are fairly randomly distributed macroscopically and microscopically. However, there are capillaries (seen at the dermis epidermis junction), venules, and arterioles, which lie closer to the dermis-subcutaneous junction. The OCT correlations of the present invention occur at depths in the skin where these blood vessels reasonably can be expected to be located. The algorithm generates an intensity difference plot to determine potential offsets that correlate closely to the selected blood glucose points.

An intensity difference plot has a characteristic peak-to-valley pattern that crosses zero at one or more certain depths. The greatest change in an intensity difference plot occurs at depths surrounding the zero-crossing point(s) in the data line. The algorithm identifies the zero-crossing point(s) and identifies localized extrema (i.e., localized minimum and maximum data points) on either side of the zero-crossing point(s). Because the range of data falling within the localized extrema surrounding the zero-crossing point(s) represents the greatest change in the data provided by the OCT scans, potential offsets that correlate closely to the selected the blood glucose points lay within this range of data. Once the algorithm identifies the localized extrema associated with the zero-crossing point(s), it determines the potential offsets. Optionally, the algorithm may include offsets within a certain variance of the localized extrema.

The percentage change in the slopes of the OCT signals for a given change in blood glucose levels depends on the sensor design. Generally, individual subjects fit within a small percentage range, which is within an order of magnitude. For a given sensor design, it is necessary to find the mean of that range and determine the standard deviation around the mean. These values are determined empirically through a calibration subset. Typically, about 30 to about 40 subjects are obtained across different age and racial demographics for a given sensor design. From that group, the algorithm would derive a filter percentage based on the mean and standard deviation about the mean. The filter percentage forms the vector for the glucose vector grid part of the algorithm. The final numbers used in the vector grid filter will depend on the sensor design. In one particular design, the relevant physiologic range of the percentage change is about 2% per 18 mg/dL to about 20% per 18 mg/dL. In other sensor designs, the mean could be higher.

In some embodiments of the present invention, in order to identify potential offset and interval combinations or pairs that closely correspond to the selected blood glucose points, the algorithm utilizes potential offsets identified from the intensity difference plot to generate a glucose vector grid he relevant physiologic range of the percentage change depends on physiologic factors as well as the size and depth of the tested region of biological tissue. The glucose vector grid is a table whose x-coordinates are the offset values and whose y-coordinates are the interval values. The calculated positive percentage changes are entered for each offset and interval pair to form the grid. Each (x, y) coordinate of the grid contains the percentage change in the signal based per 18 mg/dL of glucose. In some embodiments of the present invention, to generate the glucose vector grid, the algorithm determines the slope values for multiple combinations of intervals and potential offsets for the two selected OCT scans, using a common slope calculation, such as, for example, a linear least-squares fit calculation. The algorithm then determines the difference in the slope values for each offset and interval combination/pair between the two selected OCT scans, and represents the slope difference as a percentage change between the two selected OCT scans.

For each potential offset and interval pair, the scattering coefficient, $\mu_s$, can be determined. More specifically, in some embodiments of the present invention, a potential offset and interval pair can be chosen and the slope of the OCT scan-data line segment corresponding to the chosen offset and interval pair is computed using a common slope calculation, such as, for example, a linear least-squares fit calculation. The scattering coefficient, $\mu_s$, is proportional to the slope of the OCT scan-data line segment that corresponds to the chosen offset and interval pair, and is calculated for each of the OCT scans, which are averaged, so that the chosen offset and interval pair has a number of associated scattering coefficients, $\mu_s$, equal to the number of the multitude of OCT scans. This process then is repeated for each potential offset and interval.

The scattering coefficient, $\mu_s$, corresponding to an offset, interval pair, is proportional to an associated slope value. Estimated blood glucose levels, which are used to calibrate the OCT-based sensor, as discussed below, are related to the scattering coefficients, $\mu_s$, either proportionally or inversely proportionally. Thus, changes in the slope of an OCT signal (and thus, changes in the scattering coefficient, $\mu_s$) correlate to changes in blood glucose levels. When blood glucose levels are increasing, the scattering coefficients, $\mu_s$, decrease (i.e., the slopes of the OCT signal decrease) because the scatter of light by the biological tissue decreases. This translates into a negative percentage-change value for an increase in blood glucose levels. Accordingly, when blood glucose levels are decreasing, the scatter of the light by the biological tissue increases, and thus, the scattering coefficients, $\mu_s$, (i.e., the slopes of the OCT signal) increase. This translates into a positive percentage-change value for a decrease in blood glucose levels.

Once the algorithm has generated sets of estimated blood glucose levels, it may refine the sets of estimated blood glucose levels by applying one or more statistical filters. The order in which the statistical filters are applied may be varied. The algorithm is hard coded to make the decision of whether to accept a given offset, interval pair in the grid based on a range determined from data obtained from a large pool of subjects for a given sensor configuration. Thus, for example, the algorithm may be hard coded to choose a range of percentage-change values of about 4% to about 8% of the slope of the segment of the OCT scan line. The algorithm will generate a slope of the segment of the OCT scan line and a set of estimated blood glucose levels for each offset, interval pair that has a percentage-change value between about 4% and about 8% using all of the OCT scans taken during the specified time period.

One filtering option eliminates sets of estimated blood glucose levels that contain negative or unusually small (less than about 10 mg/dL) estimated blood glucose levels. Thus, if the calculated percentage change of a given offset, interval pair is below the established low value, that pair is discarded.

Another filtering option eliminates sets of estimated blood glucose levels that contain unusually high estimated blood glucose levels (i.e., more than about 500 mg/dL). Thus, if the calculated percentage change of a given offset, interval pair is unusually high, that pair is discarded. This leaves behind offset, interval pairs which are reasonable.

After applying at least one filter, the algorithm uses the remaining set(s) of estimated blood glucose levels to calibrate the OCT-based blood glucose monitor. The algorithm then averages the estimated blood glucose values to generate one averaged estimated blood glucose value that is associated with the new averaged OCT scan and calibrates the OCT-based blood glucose monitor with this averaged estimated blood glucose value.

For positive percentage-change values, an estimated blood glucose level is equal to the negative value of the slope value associated with the corresponding offset and interval pair. For negative percentage-change values, an estimated blood glucose level is equal to the negative inverse of the slope value associated with the corresponding offset and interval pair. Because each offset and interval pair has one associated slope value for each OCT scan, each offset, interval pair produces a set of scattering coefficients, the number of which will equal the number of (averaged) OCT scans taken during the specified time period. Optionally, depending on the tested area of the biological tissue, the algorithm may vary the range of percentage-change values in order to produce different sets of potential offset and interval pairs.

The algorithm creates a calibration curve correlating scattering coefficients and blood glucose values by performing a regression analysis, wherein each x-value comprises a scattering coefficient corresponding to the scattering coefficient of an invasively obtained blood glucose measurement and each y-value comprises the blood glucose value measured from each invasively obtained blood glucose measurement. Once the OCT data has been transformed into calibrated blood glucose levels, the "biological relevance" of the data (including, but not limited to, whether the estimated blood glucose level changed too fast to be real, whether the estimated blood glucose level is negative, or whether the estimated blood glucose level goes too high) can be determined by a simple linear regression of the paired blood glucose/OCT points. For example, one embodiment of the present invention comprises a home monitor in which the estimated blood glucose level would never reach > about 500 mg/dL. Typical blood glucose test strips do not read such a high blood glucose level.

Another aspect of the present invention includes refining the estimated blood glucose levels by calculating an average estimated blood glucose level for each point in time associated with the testing time period. The algorithm selects a first point in time and averages the estimated blood glucose levels corresponding to the first point in time at which a first (averaged) OCT scan was taken for each offset and interval pair. The algorithm then repeats the process for each point in time and generates a set of average estimated blood glucose levels equal to the number of averaged OCT scans taken. It is possible to put a repeated glucose requirement at certain intervals in the algorithm. For example, the algorithm can require a new glucose value every once an hour, as often as every estimated OCT glucose point, or every 12 hours. Generally, further calibration of the OCT-based blood glucose monitor of the present invention would not be required. However, in alternate embodiments, the algorithm is reapplied at particular intervals to recalibrate the OCT-based blood glucose monitor.

The algorithm calculates a standard deviation for each average estimated blood glucose level, uses the average estimated blood glucose level and the corresponding standard deviation for the first point in time, and compares each estimated blood glucose level from each set of estimated blood glucose levels at the first point in time. If an estimated blood glucose level at the first point in time falls outside one standard deviation of the average estimated blood glucose level, the entire set of estimated blood glucose levels and, accordingly, the corresponding offset and interval, are ignored. The algorithm repeats this process for each point in time and each corresponding average estimated blood glucose level and the associated standard deviation. The remaining set(s) of estimated blood glucose levels form a calibration data set, i.e., the estimated blood glucose levels that are within one standard deviation of the average estimated blood glucose level form a calibration data set for calibrating the OCT-based blood glucose monitor. If more than one set remains, a final calibration data set of estimated blood glucose levels is computed by taking the average of the remaining sets of estimated blood glucose levels for each point in time.

Optionally, the algorithm may calculate a median estimated blood glucose level for each point in time and may calculate corresponding standard deviation values. The algorithm then uses the median estimated blood glucose level and the corresponding standard deviation for the first point in time and compares each estimated blood glucose level from each set of estimated blood glucose levels at the first point in time. Similar to the process described above, if an estimated blood glucose level at the first point in time falls outside one standard deviation of the median estimated blood glucose level, the entire set of estimated blood glucose levels and, accordingly, the corresponding offset and interval, are ignored. The algorithm repeats this process for each point in time and each corresponding median estimated blood glucose level and the associated standard deviation. The remaining set(s) of estimated blood glucose levels form a calibration data set. If more than one set remains, a final calibration data set of estimated blood glucose levels is computed by taking the average of the remaining sets of estimated blood glucose levels for each point in time.

Optionally, the algorithm may calculate both an average estimated blood glucose level and a median estimated blood glucose level and standard deviation for each point in time and use both the average and the median estimated blood glucose levels to refine the sets of estimated blood glucose levels, as described above for each.

To apply the calibration set of estimated blood glucose levels to an OCT-based blood glucose monitor, the algorithm performs a new OCT scan at a new time. The algorithm then computes a new estimated blood glucose level for the new OCT scan using the calibration set of estimated blood glucose levels and the corresponding offset and interval pair. If more than one set of estimated blood glucose levels was used to generate the calibration set, the algorithm may use each set of estimated blood glucose levels and the associated offset and interval pairs to compute corresponding new estimated blood glucose levels, i.e., a new estimated blood glucose level for each offset and interval pair. The algorithm then averages the new estimated blood glucose levels to generate one new estimated blood glucose level for the new point in time.

According to another embodiment of the present invention, potential offsets that correlate closely to blood glucose levels may be determined by utilizing the change in the slope of the OCT scan-data line as a function of the depth of the biological tissue. Specific structures, such as blood vessels, in the biological tissue may scatter the light of the OCT scan differently than the surrounding tissue and medium and may produce discontinuities in the OCT scan data, even though the blood glucose level is not changing. The term "medium" is used herein to describe the relatively homogeneous structures in the skin, including, but not limited to, skin cells, the collagen/elastin fiber matrix, interstitial fluid, and the like. An object, including but not limited to a blood vessel, has a very different scattering profile than this medium. This different scattering profile provides a characteristic signal that can be used to identify the tissue depth at which the scattering will correlate to glucose.

The term "discontinuity" as used herein refers to an identifiable, abrupt change in the OCT scan line indicating a tissue interface transition. Most simply, a discontinuity appears as a "bump" on the slope of an otherwise straight line. For example, in FIG. 1, at about 2.9 on the depth scale, a bump, which is a discontinuity in the line, is associated with a blood vessel. The presence of, a tissue interface transition, for example, a blood vessel, therefore causes an abrupt change in the intensity, Such discontinuities allow the algorithm to identify potential offsets that correlate closely (>95% confidence level) to blood vessels.

According to one aspect of the present invention, the algorithm may identify the discontinuities in the OCT scan-data lines by computing the second derivative of the OCT scan data and then computing the squared value of the second derivative. The discontinuities, which may not be visible initially in an intensity plot, are enhanced by calculating the second derivative of the OCT scan data. Squaring the data results of the second derivative calculation ensures that the resulting data results are positive. Because the discontinuities are enhanced, the discontinuities are visible as "spikes" or bumps along the new OCT scan-data line. Offsets that correspond to the discontinuities represent points along the OCT scan-data line closely correlated to blood vessels. The algorithm identifies offsets that correspond to the discontinuities and generates a glucose vector grid, as discussed above. Optionally, the algorithm may utilize both an intensity difference plot and a second derivative plot to identify potential offsets.

Once the algorithm has identified acceptable offset, interval pairs and generated the appropriate calibration factors, every time the calibrated OCT-based blood glucose monitor is employed to generate a new OCT scan, the algorithm will apply the acceptable offset, interval pairs and calibration factors to subsequent scans.

In some embodiments of the present invention, the Pearson's correlation method (i.e., the "Pearson Product Moment Correlation" method, often referred to as "Pearson's correlation coefficient") is used to determine the degree of a linear relationship between the scattering coefficients, $\mu_s$, and the measured blood glucose levels. Changes in the slopes of the OCT scan-data line, i.e., changes in the scattering coefficients, $\mu_s$, are either proportionally related or inversely proportionally related to changes in the level of blood glucose. By using the Pearson's correlation coefficient to determine which scattering coefficients, $\mu_s$, closely correlate to the measured blood glucose levels, the algorithm may determine an optimal offset and interval pair to choose for calibrating the OCT-based monitor.

The Pearson's correlation coefficient ranges between minus 1.0 (−1.0) to positive 1 (+1.0). A coefficient value of +1.0 indicates a perfect correlation between two variables, that is, a perfect positive linear relationship exists between the two variables. The linear relationship is usually represented by a scatter plot (meaning a visual display showing the numerical data of one variable plotted against the numerical data of a second variable where each data point has a coordinate on a horizontal and vertical axis). A perfect correlation coefficient value of +1.0 also indicates that as values of one variable increase, e.g., along an x-axis, values of the other variable increase correspondingly, e.g., along a y-axis, and all values lie along a single line. A Pearson's correlation coefficient value of −1.0 indicates a perfect inverse linear relationship between two variables, that is, as values along the x-axis increase, values along the y-axis decrease correspondingly. A Pearson's correlation coefficient value of 0.0 indicates that no correlation exists between the two variables, i.e., the values are so scattered that it is impossible to determine a linear relationship between values for the two variables.

In some embodiments of the present invention, a Pearson's correlation coefficient is generated to correlate the scattering coefficients associated with each potential offset, interval pair to the measured blood glucose levels. The process is repeated for each potential offset, interval pair in order to generate a set of Pearson's correlation coefficients. The Pearson's correlation coefficients then may be represented graphically as a contour plot against the potential offset and interval pairs. Offset and interval pairs that produce Pearson's correlation coefficients at or near a value of +1.0 (i.e., high positive Pearson's correlation coefficient values) indicate that the scattering coefficients, Us, associated with the slopes, which are derived from a linear fit corresponding to offset, interval pairs, correlate closely to the measured blood glucose levels. In other words, for a given set of blood glucose levels and an associated set of scattering coefficients, $\mu_s$, high positive Pearson's correlation coefficients indicate a constant linear relationship between the two sets of data, and, accordingly, a close correlation. The algorithm may select a preferred range of Pearson's coefficient values in order to select corresponding offset, interval pairs for calibrating the OCT-based blood glucose monitor.

Additionally, offset, interval pairs that have Pearson's coefficient values at or near a value of −1.0 (i.e., a high negative Pearson's correlation coefficient) also represent areas where the scattering coefficients, $\mu_s$, associated with the offset, interval pairs closely correlate to the measured blood glucose levels. A high negative Pearson's correlation coefficient indicates that the scattering coefficients, $\mu_s$, associated with the slopes, which are derived from a linear fit corresponding to offset, interval pairs, are closely correlated to the measured blood glucose values, but that the slope values, and, therefore, the scattering coefficients, $\mu_s$, are negative. The offset, interval pairs that produce high negative Pearson's correlation coefficients also may be used to calibrate the OCT-based blood glucose monitor. The range of preferred Pearson's correlation coefficients is adjustable according to the needs of the algorithm. All other offset, interval pairs that do not produce a Pearson's correlation coefficient within such preferred range(s) are ignored.

To calibrate the OCT-based blood glucose monitor, the algorithm selects an offset, interval pair with a desired Pearson's correlation coefficient, and calculates the scattering coefficient, $\mu_s$, for each portion of each averaged OCT scan-data line that corresponds to the selected offset, interval pair. The scattering coefficients, $\mu_s$, corresponding to the selected offset, interval pair are plotted with the measured blood glucose levels against the specified time period to display how closely correlated the OCT-based blood glucose monitor data is to the measured blood glucose value or level. If the algorithm is satisfied with the correlation, it may calibrate the OCT-based blood glucose monitor according to the scattering coefficients, $\mu_s$, associated with the selected offset, interval pair in order to compute estimated blood glucose levels. The terms "estimated" and "predicted" are used interchangeably herein. An estimated blood glucose level is computed by taking the negative of the scattering coefficient value for the selected offset, interval pair. For a selected offset, interval pair that has an anti-correlated scattering coefficient value, a corresponding estimated blood glucose level is computed by taking the negative inverse of the scattering coefficient value.

If the algorithm is not satisfied with the correlation produced by the selected offset, interval pair, it may select another offset, interval pair according to the corresponding Pearson's correlation coefficient until a desired result is reached. Once the algorithm has identified acceptable offset, interval pairs and generated the appropriate calibration factors, every time the calibrated OCT-based blood glucose monitor is employed to generate a new OCT scan, the algorithm will apply the acceptable offset, interval pairs and calibration factors to subsequent scans.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs.

Any methods and materials similar or equivalent to those described herein also can be used in the practice or testing of the present invention.

All publications mentioned herein are incorporated herein by reference to disclose and describe the methods and/or materials in connection with which the publications are cited.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

FIG. 1 shows an intensity profile of light scattered from a biological tissue (human skin) as measured via an OCT-based blood glucose monitor according to an embodiment of the present invention. If an appropriate wavelength of light is chosen (e.g., about 1300 nanometers) such that the absorption coefficient of the light, $\mu_a$, is small relative to the scattering coefficient of the light (for example, if the scattering coefficient is five times the absorption coefficient), $\mu_s$, by the biological tissue, then a change in the slope of the OCT scan-data line likely will be dominated by glucose-induced changes in the tissue scattering. Based on the wavelength of light chosen, the OCT-based blood glucose monitor signal spikes at certain regions of the surface of the biological tissue and then falls dramatically within the epidermis region of the skin. The OCT scan-data line then rises and slowly decreases within the dermis region as the depth of light in the biological tissue (e.g., skin) increases. Because most blood vessels are located in the dermis region, it is this portion of the OCT scan-data line that provides data for calibrating the OCT-based blood glucose monitor. As shown in FIG. 1, the slope of the OCT scan-data line may increase or decrease relative to the blood glucose level. That is to say, the slope of the OCT scan-data line decreases as the blood glucose level increases, and, accordingly, the slope of the OCT scan-data line increases as the blood glucose level decreases.

Figure 2:
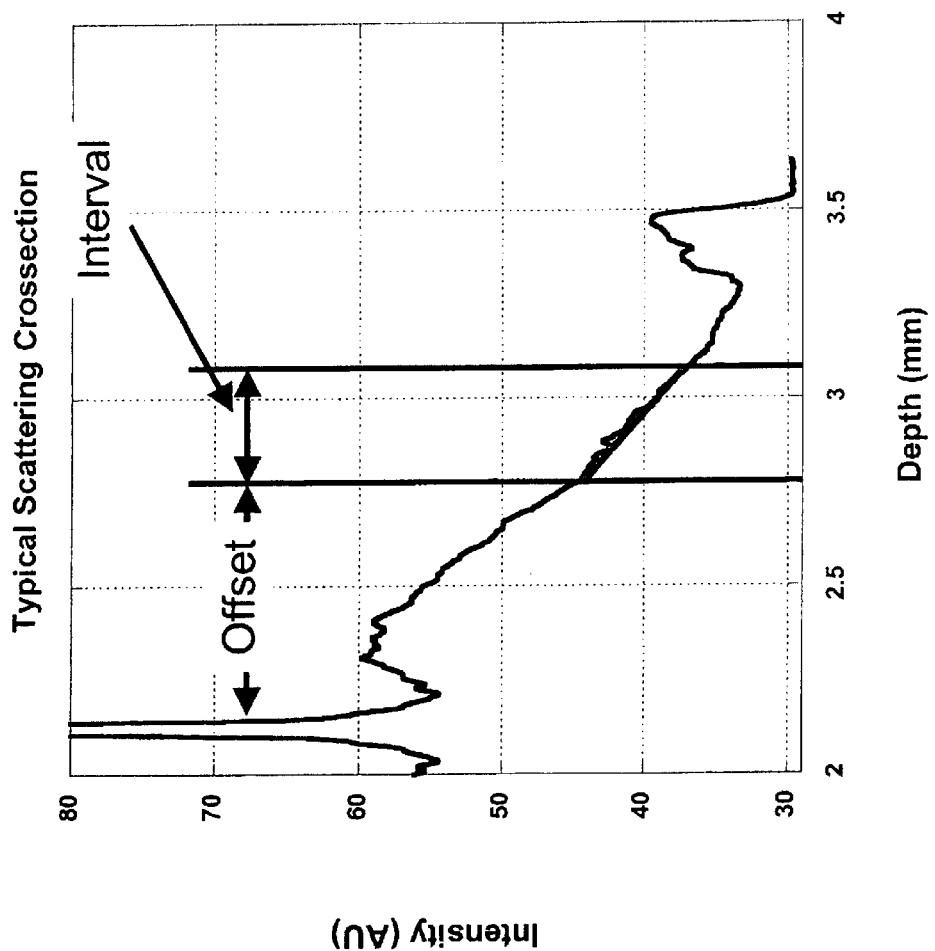
FIG. 2 illustrates how an offset and an interval are defined, according to an embodiment of the present invention.

FIG. 2 illustrates the two parameters used to maximize the correlation between the OCT-based blood glucose monitor data and the measured blood glucose levels. The first parameter, the offset, is the depth at which to begin determination of the correlation of the OCT scan-data line to the measured blood glucose levels. The offset is measured from the spike in the OCT scan-data line, which represents the surface of the biological tissue (e.g., skin) to a particular depth within the dermis layer of the biological tissue (e.g., skin). The second parameter, the interval, is the portion of the OCT scan-data line used to correlate the OCT data to the measured blood glucose levels. The interval is measured from the offset depth and can be any length according to the algorithm's needs; for example, the length can range from a value about equal to the difference between adjacent points of the OCT scan-data line (which approximates the derivative of the line) to about 1 mm (used with a linear least squares fit calculation to find the slope). Given the depth of the entire OCT signal, there are multiple combinations of offsets and intervals that may be used for correlating the OCT data. For example, three offset, interval pairs may be: an offset of about 300 microns and an interval of about 50 microns; an offset of about 300 microns and an interval of about 150 microns; and an offset of about 700 microns and an interval of about 100 microns.

Figure 3A:
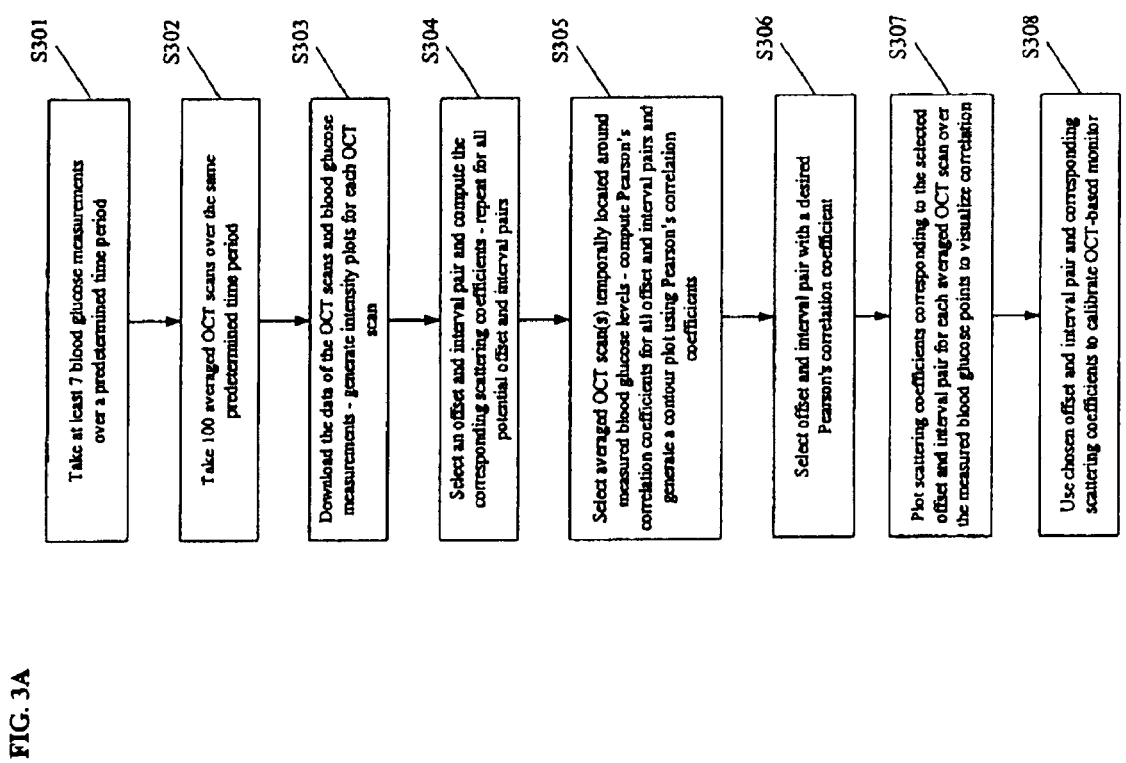
FIGS. 3A and 3B illustrates a process flow of a method for calibrating an OCT-based blood glucose monitor, according to embodiments of the present invention.
Figure 3B:
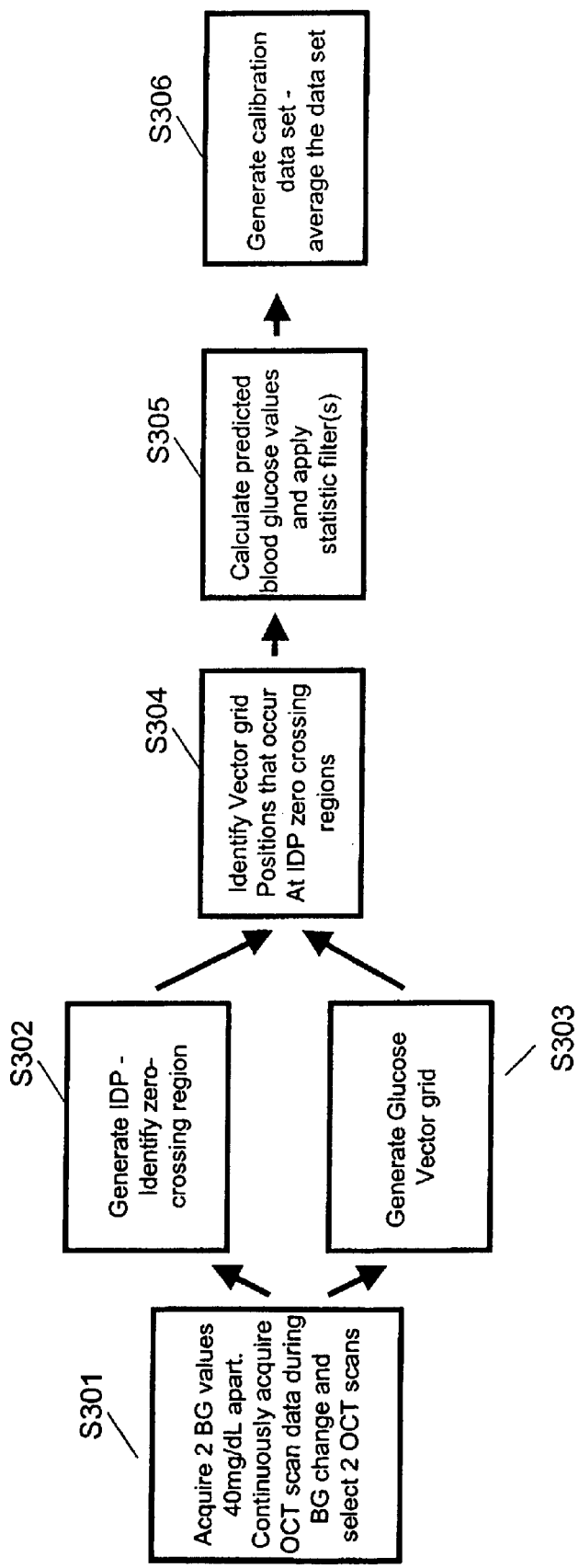

In some embodiments of the present invention, the method for reducing the amount of data necessary to calibrate an OCT-based blood glucose monitor is as summarized in the flow chart shown in FIG. 3. FIG. 3, together with the graphs of FIG. 4 and FIG. 5, presents a process flow of a method for maximizing the correlation between the OCT-based blood glucose monitor data and measured blood glucose levels, and using that correlation to calibrate the OCT-based blood glucose monitor, according to an embodiment of the present method. The steps of the method need not be taken in the sequence illustrated. As shown in FIG. 3*b*, Step S302 may be implemented at the same time as Step S303, i.e., they need not be run sequentially, as shown in FIG. 3*a*. Over a period of time, a user takes a number of invasively-obtained blood glucose measurements (see e.g., S301 of FIG. 3) to measure the level of blood glucose over a given period of time, for example, 190 minutes. Since a glucose change must be recorded in the blood glucose levels by both conventional blood glucose chemistry and the OCT value for correlation purposes, given that the maximum a human subject's blood glucose can change is about 5 mg/dL per min (average is about 2 mg/dL) it would take about 4 minutes to about 10 minutes to get a reasonable blood glucose spread in values.

A minimum of two invasively obtained blood glucose measurements (or points) is required for the IDP/glucose vector grid approach as described above, although more measurements can be used. In the Pearson approach, a minimum of seven invasively obtained blood glucose measurements (or points) is needed for statistical confidence. In some embodiments of the present invention, the time period includes a blood glucose altering event, such as, but not limited to, subject-initiated events, e.g., eating a meal, administering insulin, drinking a beverage containing sugar (e.g., juice) and the like. It is understood that one or more blood glucose altering event also can occur on its own.

Over the same period of time (e.g., 190 minutes), the algorithm takes multiple OCT scans using the OCT-based blood glucose monitor such as, for example, about 100 OCT to about 1500 scans for a 190-minute period (S302 of FIG. 3). Although the number of OCT scans taken is at the discretion of the algorithm, the number of OCT scans taken cannot be less than the number of blood glucose measurements taken during the time period. Each OCT scan is an average of a number of OCT scans, for example, about 1500 OCT scans, in order to reduce the effects of any noise or speckle produced by the OCT-based blood glucose monitor.

Once the blood glucose measurements and OCT scan data are acquired (S301 of FIG. 3), the algorithm selects two invasively obtained measured blood glucose levels, or points, that are at least 40 mg/dL apart in value. The algorithm also selects two OCT scans that correspond to points in time of the selected blood glucose points. The algorithm creates an intensity difference plot (IDP) by calculating the difference between the data of the two selected OCT scans (S302 of FIG. 3)) FIG. 4 shows an example of an intensity difference plot according to the present invention. In FIG. 4, the algorithm has selected invasively obtained measured blood glucose point 2 (BG #2) and invasively obtained measured blood glucose point 5 (BG #5) to calibrate the OCT-based blood glucose monitor. The algorithm then selects two OCT scans that correspond to points in time of BG #2 and BG #5 and computes the difference in the data between the two selected OCT scans. The algorithm identifies one or more zero-crossing points in the intensity difference plot as well as localized extrema surrounding the zero-crossing points, respectively. The intensity difference plot in FIG. 4 has one zero-crossing point, which is located at a depth of about 225 microns. A local maximum data point is located at about 200 microns and a local minimum point is located at about 350 microns. The depths within the region of the localized extrema represent potential offsets that are closely correlated to the selected blood glucose points and are represented in FIG. 4 by a shaded box. Optionally, the algorithm may expand the box to include potential offsets within a variance amount of the localized extrema. For example, in FIG. 4, the range of potential offsets includes offsets from about 175 microns to about 400 microns.

Next, the algorithm takes the range of potential offsets from the intensity difference plot and generates a glucose vector grid, which produces potential offset and interval pairs that closely correlate to the selected blood glucose points. (See, S303 of FIG.3). Every offset, interval pair has an associated slope value for each OCT scan. The slope value is determined using a common calculation, such as, for example, a linear least squares fit calculation. Utilizing the two selected OCT scans, the algorithm calculates two slope values for each potential offset and interval pair and then calculates the difference in the two slope values as a percentage change from the OCT scan that occurs earlier in the testing time period to the OCT scan that occurs later in the testing time period. The percentage-change values (or percent signal change values) are tabulated against the corresponding offset, interval pairs.

As shown in step S304 of FIG. 3, the algorithm identifies the percentage-change values that fall within a certain physiological range predetermined by the algorithm for a particular sensor design. The range is set based on the sensor's measured response as measured in a population of a representative set. For example, in one particular sensor design, changes in blood glucose levels range from about 2% to about 20% for every 18 mg/dL. For this sensor design, the algorithm may identify percent signal change values that fall within the range of about 2% and about 20% and ignore offset and interval pairs that do not correspond to this range. Alternatively, the algorithm may minimize the range to isolate a smaller number of potential offset, interval values.

Additionally, when the algorithm takes the range of potential offsets from the intensity difference plot and generates a glucose vector grid (S303 of FIG. 3), it may generate a glucose vector grid for offset, interval pairs that have negative percentage-change values. In such an embodiment of the present invention, the algorithm may apply an alternate physiological range of percentage-change values, such as, for example, −20% to −2%, to reduce the number of potential offset, interval pairs that closely correlate to the selected blood glucose points (see e.g., S304 of FIG. 3). An example of a glucose vector grid for offset, interval pairs with negative percentage-change values is presented in FIG. 5.

The slope values of the identified offset, interval pairs are converted into estimated blood glucose values (S305 of FIG. 3). For example, if the first invasively obtained measured blood glucose point, BG #2, was measured at about 100 mg/dL and the algorithm selected a range of offset and interval pairs with percentage-change values between about minus 10.00 (−10.00) to about minus 10.20 (−10.20), then using the glucose vector grid in FIG. 5, this range of percentage-change values would correspond to four offset and interval pairs, (1) about 175 microns and about 100 microns, (2) about 175 microns and about 125 microns, (3) about 225 microns and about 75 microns, and (4) about 250 microns and 50 microns, respectively. This translates into generating sets of estimated blood glucose values for each of the four offset, interval pairs. In this example, the scattering coefficient, $\mu_s$, for each of the four offset, interval pairs is calculated and associated with the fist invasively obtained measured blood glucose point BG #2 of about 100 mg/dL taken at the first point in time as a baseline. Scattering coefficients, $\mu_s$, then are computed for all the OCT scans taken after the first point in time for each offset, interval pair. Since the percentage-change value is negative for each offset, interval pair, estimated blood glucose values are computed by taking the negative inverse of each scattering coefficient, $\mu_s$. This computation produces four sets of estimated blood glucose levels, which are used to calibrate the OCT-based blood glucose monitor. The algorithm may further refine the four sets of estimated blood glucose values by ignoring sets that contain negative estimated blood glucose levels and/or sets with estimated blood glucose levels that are below a predetermine cutoff level or above a predetermined cutoff level. The algorithm then may generate a calibration set of estimated blood glucose levels using the remaining set of estimated blood glucose levels. If more than one set remains, the algorithm may average the estimated blood glucose levels at each point in time to produce a calibration set of estimated blood glucose levels.

In some embodiments of the present invention, the algorithm can refine further the set of estimated blood glucose levels prior to generating a calibration set by, for example, and without limitation, applying statistical filters (see, e.g., S305 of FIG. 3). The order in which the statistical filters are applied may be varied. In one embodiment, the algorithm selects the estimated blood glucose levels from the potential offset, interval pairs that correspond to the first point in time and calculates an average estimated blood glucose level. The algorithm also may calculate a median estimated blood glucose level corresponding to the first point in time. For example, if the algorithm has reduced the potential offset, interval pairs to four (4) pairs, as previously described, then for a first point in time, the algorithm averages the four estimated blood glucose levels. The algorithm then repeats this process for each point in time to generate a set of average estimated blood glucose levels and calculates a standard deviation for the set of average estimated blood glucose levels. Accordingly, the algorithm may generate a set of median estimated blood glucose levels and a standard deviation. The algorithm then refines the set of estimated blood glucose levels by ignoring sets of estimated blood glucose levels that fall outside one standard deviation of the average estimated blood glucose level at any point in time and/or one standard deviation of the median estimated blood glucose level at any point in time.

Alternately, in another embodiment, to further refine the set of estimated blood glucose levels prior to generating a calibration set (see, e.g., S305 of FIG. 3), the algorithm may apply the computed average and median estimated blood glucose levels to refine the set of estimated blood glucose levels using either or both of the following equations:

$$BG_{Avg.} - A*BG_{Avg.\ S.D.} \leq BG \leq BG_{Avg.} + A*BG_{Avg\ S.D.} \quad (1)$$

$$BG_{Median} - A*BG_{Median\ S.D.} \leq BG \leq BG_{Median} + A*BG_{Median\ S.D.} \quad (2)$$

Where "$BG_{Avg.}$" is the computed average estimated blood glucose level at a point in time, "$BG_{Avg.\ S.D.}$" is the computed standard deviation of the set of averaged estimated blood glucose levels, "BG" is a particular estimated blood glucose level at any point in time, A is a filter variable with a range of about 0.1 to about 1, "$BG_{Median}$" is the computed median estimated blood glucose level at a point in time, and "$BG_{Median\ S.D.}$" is the computed standard deviation of the set of median estimated blood glucose levels. The filter variable, A, allows the algorithm to take less than the standard deviation, if desired. The above equations allow the algorithm to ignore sets of estimated blood glucose levels that are outside a range corresponding to less than one standard deviation.

The algorithm is left with one or more sets of estimated blood glucose levels and corresponding offset and interval pairs to be used to calibrate the OCT-based sensor (see e.g., S306 of FIG. 3). The algorithm then averages the sets of estimated blood glucose levels for each point in time to generate a calibration set of estimated blood glucose levels, and applies the calibration set to calibrate the OCT-based blood glucose monitor.

FIGS. 6A and 6B are flow charts summarizing methods of the present invention for reducing the data necessary to calibrate an OCT-based blood glucose monitor, where the methods have been modified from the method of the present invention summarized in the flow chart of FIG. 3. In both FIGS. 6A and 6B, the algorithm takes a number of blood glucose measurements over a period of time. In some such embodiment, the time period includes a meal. Over the same period of time, the algorithm takes multiple OCT scans using the OCT-based blood glucose monitor. Once the blood glucose measurements and OCT data is acquired (S301), the algorithm selects two measured blood glucose levels, or points, that are at least about 40 mg/dL apart in value. The algorithm also selects two OCT scans that correspond to points in time of the selected blood glucose points.

In FIG. 6A, S601, the algorithm generates a second derivative plot to enhance discontinuities in each selected OCT scan-data line. As discussed above, and without being held to any particular theory, the discontinuities likely correlate to a tissue interface transition, such as, but not limited to blood vessels, and an area in the biological tissue comprising such tissue interface transitions is the preferred area of the biological tissue for measuring the level of blood glucose. By emphasizing the discontinuities, the locations in depth of the tissue interface transitions may be identified. Thus, the algorithm generates the second derivative plot to identify potential offsets that correlate closely to blood vessels. The method according to FIG. 6A follows the method of FIG. 3 after S601 (i.e., S303-S306 in FIG. 3 are used in the method of FIG. 6A).

The method summarized in the flow chart in FIG. 6B combines the methods summarized in the flow charts of FIG. 3 and FIG. 6A. That is to say, the algorithm creates both an intensity difference plot (S302 of FIG. 3) and a second derivative plot (S601 of FIG. 6A). The algorithm then identifies potential offsets by using the region created around the zero-crossing point in the intensity difference plot and the discontinuities identified in the second derivative plot (see, e.g., S602 of FIG. 6B). The method according to FIG. 6B otherwise follows the method of FIG. 3 (see, e.g., S301, S303, and S305-S306).

Figures 7A, 7B:
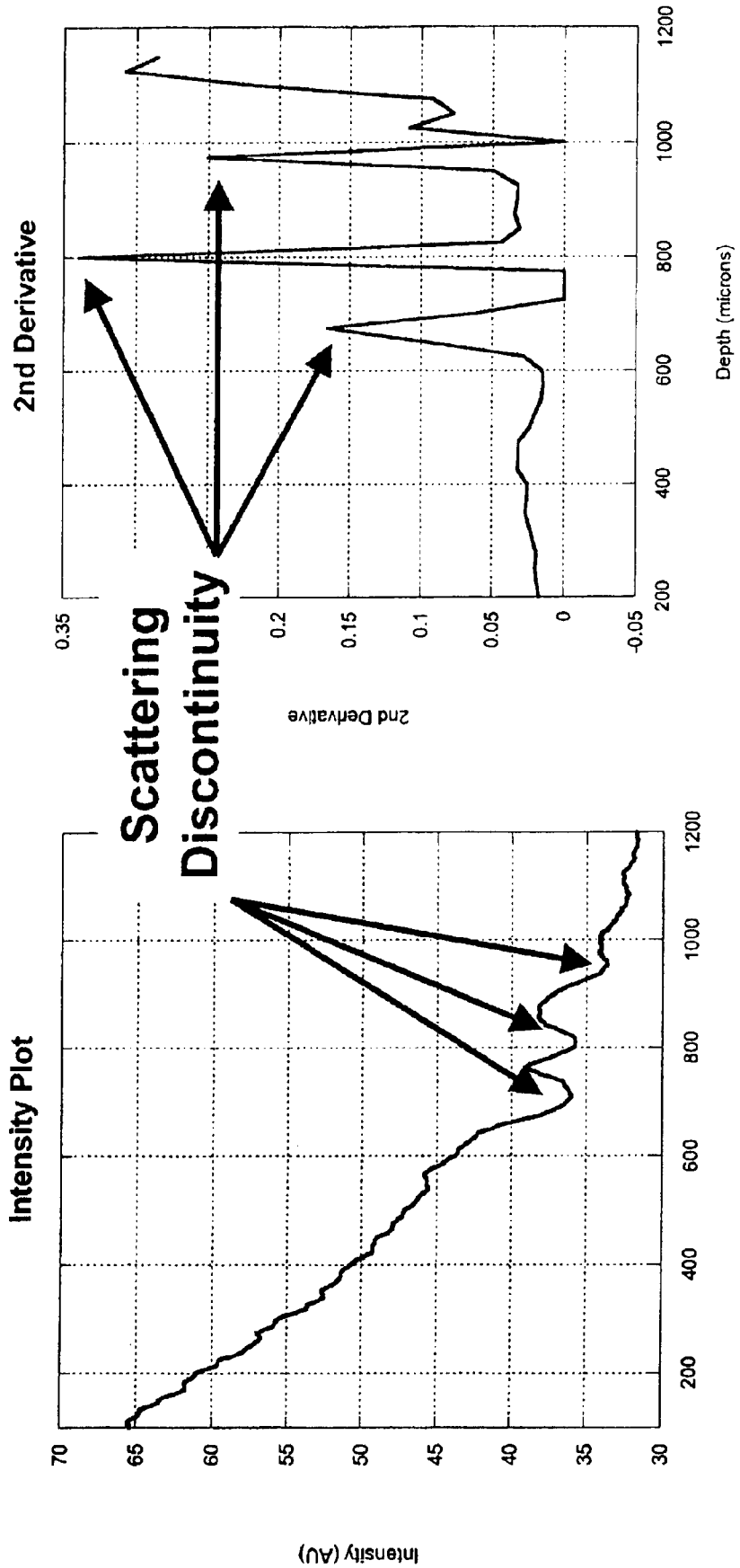
FIGS. 7A and 7B are graphical illustrations in which scattering discontinuities are identified, according to an embodiment of the present invention.

FIGS. 7A and 7B graphically illustrate how a second derivative plot enhances discontinuities in the OCT scan-data line, referred to as the scattering profile. In FIG. 7A, an OCT scan-data line is plotted against the depth of the scanned biological tissue. Discontinuities in the OCT scan-data line are identified by circles in the graph; however, the discontinuities may be difficult to visualize. In FIG. 7B, a square of a second derivative of the OCT scan-data line is plotted against the depth of the scanned biological tissue. The discontinuities in the OCT scan-data line are enhanced by the second derivative computation while calculating the square value of the second derivative removes any negatives that may exist. The discontinuities correspond to changes in blood glucose levels and indicate potential offsets that closely correlate to tissue interface transitions, such as blood vessels.

Figure 8:
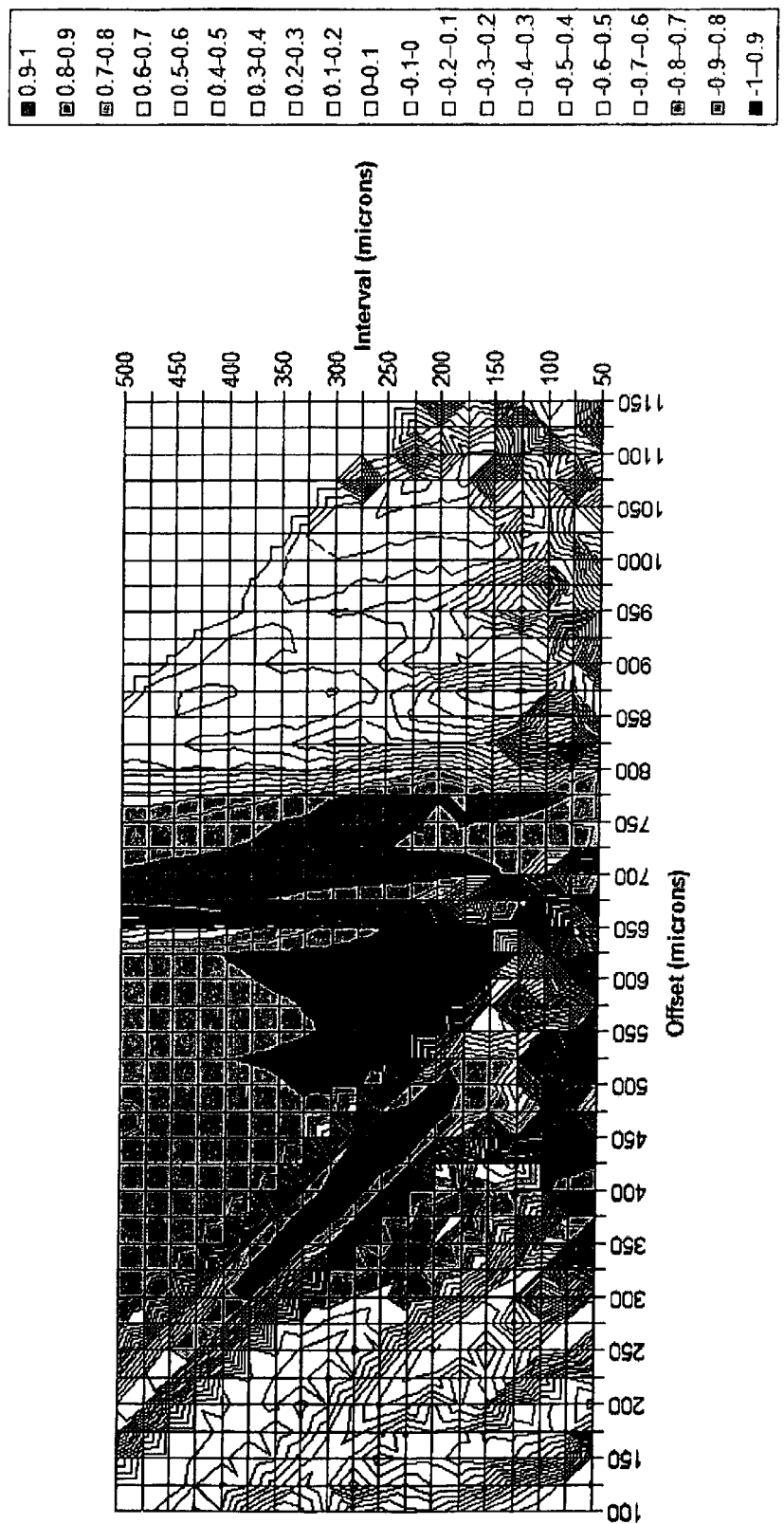
FIG. 8 is contour plot illustrating Pearson's correlation coefficients calculated for multiple pairs of offsets and intervals, according to an embodiment of the present invention.
Figure 9:
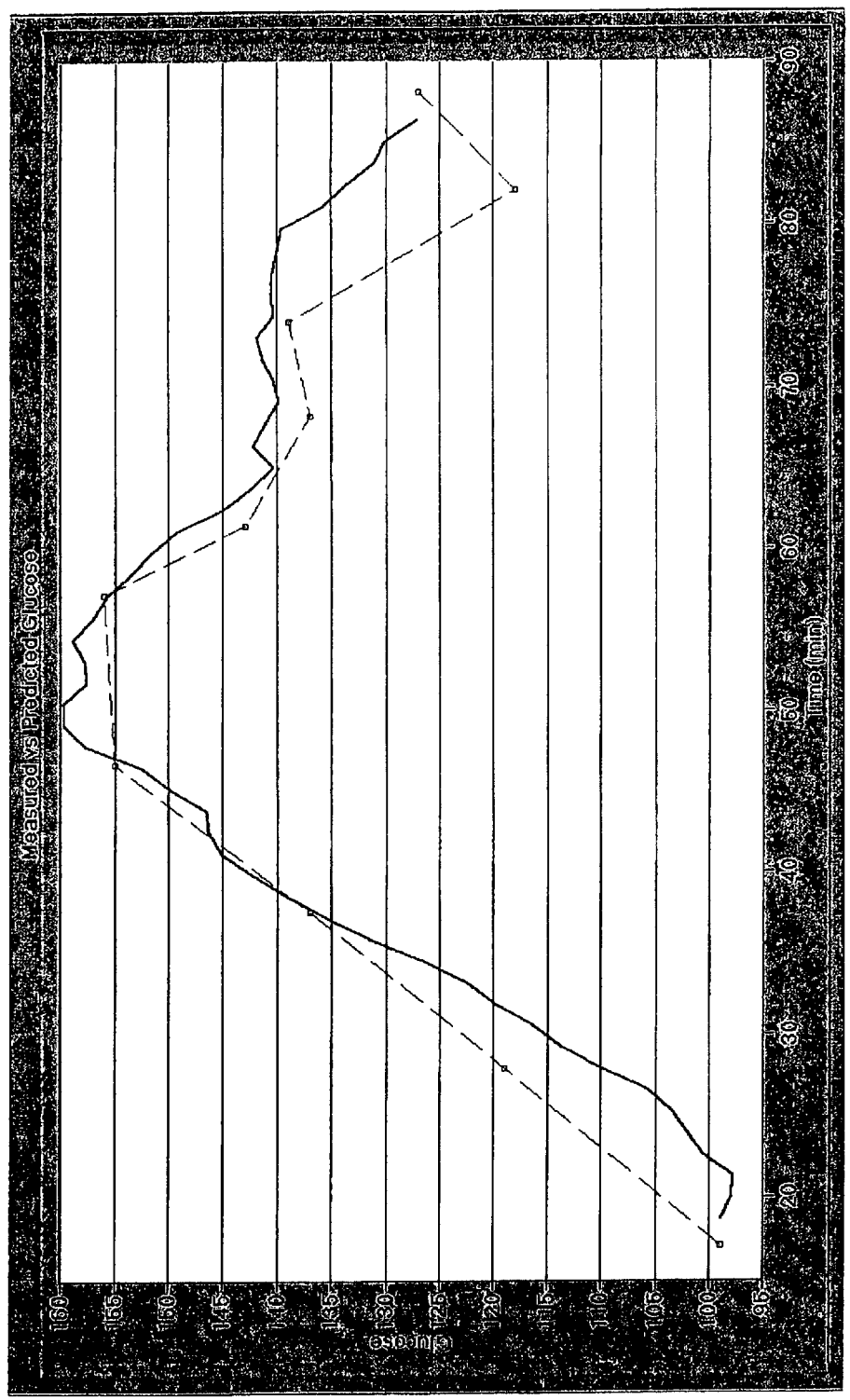
FIG. 9 is a graphical illustration of estimated blood glucose levels with a high correlation between an OCT signal and measured blood glucose levels, according to an embodiment of the present invention.
Figure 10:
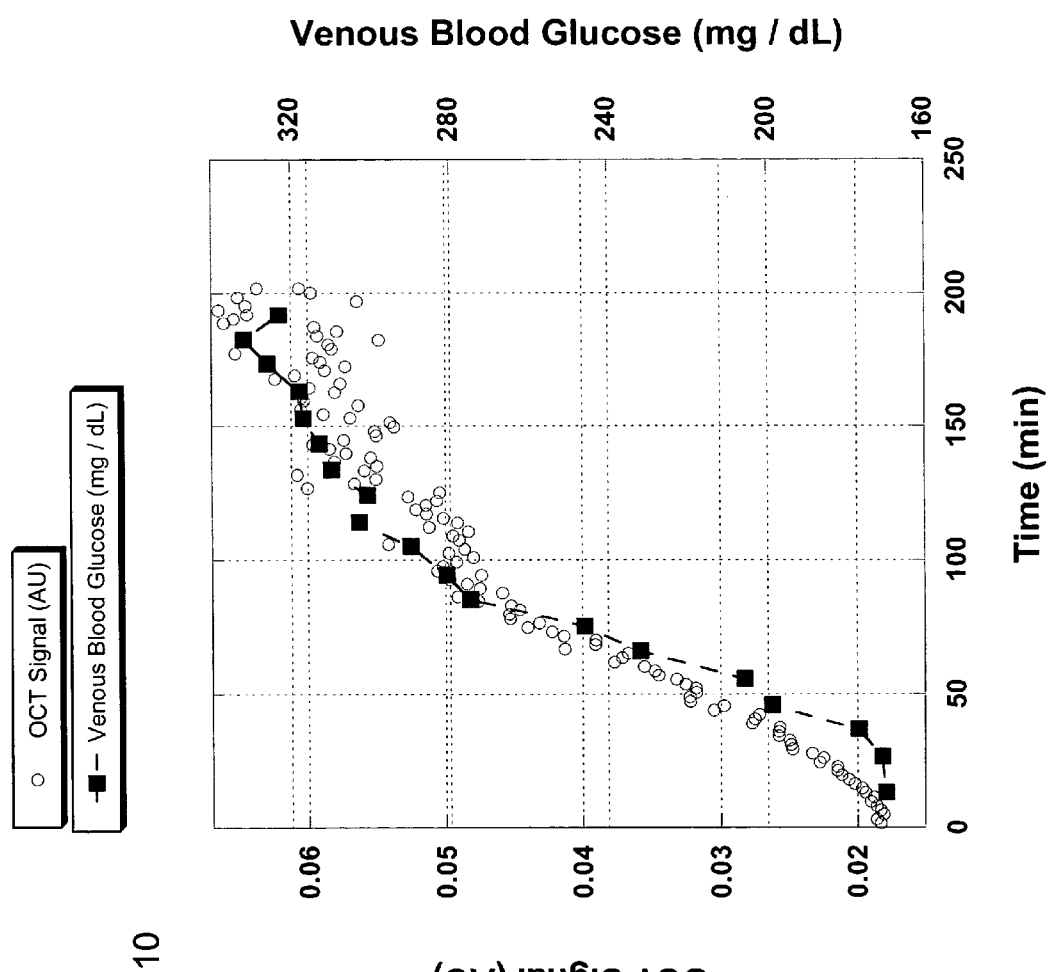
FIG. 10 is a graphical correlation between a high an OCT signal and measured blood glucose levels.

FIG. 8 is an example of a calibration set of estimated blood glucose levels generated by using the method described in FIG. 3. Although the method utilizes two measured blood glucose points, FIG. 8 includes an additional eight measured blood glucose points to emphasize the close correlation between the estimated blood glucose levels and the measured blood glucose points.

According to another aspect of the present invention, a programmable computer for use in calibrating an OCT-based blood glucose monitor is provided. The programmable computer includes at least one memory having at least one region for storing computer-executable program code, and a processor for executing the program code stored in the memory. The program code includes modules for performing the slope calculations and determining a maximum correlation between the OCT scan data and the measured blood glucose levels. Slope can be calculated in many ways, including, but not limited to, linear regression. The averaged OCT scan lines are generated by adding the individual scans together and then dividing by the number of scans. Optionally, the programmable computer plots the scattering coefficients of the light, $\mu_s$, against the measured blood glucose levels. In some embodiments, the programmable computer of the present invention functions to calibrate the OCT-based blood glucose monitor. As used herein, the term "memory" refers to an electronic computer memory. The term "computer-executable program code" as used herein refers to code, such as assembly code, or another higher level language compiled into machine languages, such as C. The term "processor" as used herein refers to a computer microprocessor, such as a Pentium chip. The term "modules" refers to modular software components. The term "calculations" refers to linear least square fit, calibration, an IDP calculation and the like. The term "functions" refers to individual software components that do one form of calculation, such as addition, or something more complex, such as a linear regression.

In some such embodiments, an algorithm utilizes a computer for generating a glucose vector grid of the present invention, For example, when the algorithm takes the range of potential offsets from the intensity difference plot and generates a glucose vector grid (S303 of FIG. 3B), the algorithm may download the OCT scan data into a computer and may enter the measured blood glucose levels. Upon doing so, the algorithm may program the computer to generate intensity plots of each averaged OCT scan over time to visualize the results (see, e.g., the plots shown in FIGS. 1 and 2). The algorithm then may manually select potential pairs of offsets and intervals for continuing the correlation and calibration process, or the algorithm may program the computer to automatically select potential pairs of offsets and intervals in order to automate the process. At S304 of FIG. 3B, the scattering coefficient, $\mu_s$, is computed for each averaged OCT scan at a particular offset, interval pair. For example, given the numbers in the above example, each offset, interval pair is associated with 100 averaged OCT scans, and, thus, has 100 corresponding scattering coefficients, $\mu_s$. The scattering coefficients, $\mu_s$, then may be stored in computer-readable memory for later use.

When slope values of the identified offset, interval pairs are converted into estimated blood glucose values (S305 of FIG. 3B), the algorithm selects an averaged OCT scan temporally located around a blood glucose measurement, and instructs the computer to compute the Pearson's correlation coefficient for each potential offset and interval pair taken from the OCT scan. A contour plot is generated to visualize the Pearson's correlation coefficients in relation to each offset, interval pair, for example, as shown in FIG. 4. In FIG. 4, the x-axis represents the potential offsets, starting at about 100 microns, and the y-axis represents the potential intervals, starting at about 50 microns and increasing to about 500 microns. From the plot generated (S305 of FIG. 3B), the regions of highest correlation can be seen. From the plot of FIG. 4, the algorithm may choose one or more offset and interval pairs with a desired Pearson's correlation coefficient to calibrate the OCT-based sensor (see e.g., S306 of FIG. 3B).

The algorithm then may generate a contour plot for the measured blood glucose levels and the averaged OCT scans temporally located near the measured blood glucose level. For example, given eight measured blood glucose levels, the algorithm may select eight OCT scans corresponding in time to the eight measured blood glucose levels. The algorithm calculates slopes associated with offset, interval pairs for each of the selected OCT scans. Thus, the algorithm generates sets of eight slopes for each potential offset, interval pair. Correlating the sets of eight slopes to the eight measured blood glucose values, the algorithm generates a contour plot of Pearson's correlation coefficients corresponding to the offset, interval pairs from the selected eight OCT scans and eight measured blood glucose levels to reduce the number of potential offset, interval pairs for calibrating the OCT-based blood glucose monitor. Optionally, the algorithm may choose several OCT scans temporally located near [need to define what you mean by temporally near-within 5 minutes, for example?] a measured blood glucose level and average the slopes of the OCT scans for each offset, interval pair. The algorithm then uses the averaged slopes to compute the Pearson's correlation coefficients. For example, the algorithm may select three OCT scans temporally located around one measured blood glucose level and average the slopes of the three OCT scans to obtain an averaged slope value for each offset, interval pair. The algorithm then computes Pearson's correlation coefficients using the averaged slope values and the measured blood glucose level for multiple offset, interval pairs, and repeats the process of using three OCT scans temporally located around each measured blood glucose level.

By utilizing the Pearson's correlation method, the algorithm is able to maximize the correlation between the OCT scan data and the measured blood glucose levels and may choose an offset, interval pair and the corresponding scattering coefficients, $\mu_s$, that closely imitate the variations in the actual blood glucose levels (see, e.g., S306 of FIG. 3B). For example, an algorithm may select one or more offset, interval pairs with Pearson's correlation coefficients between about 0.8 and about 1.0, and between about minus 0.8 (−0.8) and about minus 1.0 (−1.0). If the algorithm wishes to narrow the correlated offset and interval pairs, the algorithm may narrow the range of useful Pearson's correlation coefficients, such as, for example, to a range of about 0.9 to about 1.0, and a range of about minus 0.9 (−0.9) to about minus 1.0 (−1.0). As discussed above, high negative Pearson's correlation coefficients represent a close correlation between the OCT scan data and the measured blood glucose levels, but differ from positive Pearson's correlation coefficients in that the negative values represent that the change in the slope of the OCT signal is decreasing as the change in the blood glucose level is increasing.

As shown in S307 of FIG. 3B, the algorithm selects an optimal offset, interval pair using the generated contour plot(s) and instructs the computer to generate a plot of the scattering coefficients corresponding to the selected offset, interval pair for all of the averaged OCT scans taken during the testing time period, over the measured blood glucose levels. FIG. 5 illustrates a plot of scattering coefficients corresponding to one optimal offset, interval pair compared to measured blood glucose levels. In FIG. 5, nineteen blood glucose measurements were taken over a 190-minute time period, as shown by each black square. The rise and fall in the blood glucose line is due to the subject ingesting food during the 190-minute time period. Each circle corresponds to a scattering coefficient, $\mu_s$, computed from the slope associated with the selected offset, interval pair, for an averaged OCT scan. In FIG. 5, scattering coefficients, $\mu_s$, corresponding to about 125 averaged OCT scans, are represented by the circles. As shown in FIG. 5, the scattering coefficients associated with the chosen offset, interval pair correlate closely (i.e., >95% confidence level) to the measured blood glucose levels.

Accordingly, at S308 of FIG. 3B, the algorithm then uses the chosen offset and interval and corresponding scattering coefficients, $\mu_s$, to calibrate the OCT-based blood glucose monitor. To calibrate the OCT-based blood glucose monitor, estimated blood glucose levels are calculated by taking the negative of the scattering coefficient values for positively correlated scattering coefficients, $\mu_s$. For anti-correlated scattering coefficients, estimated blood glucose levels are calculated for the selected offset and interval pair.

While the present invention has been described with respect to what are some embodiments of the invention, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A noninvasive method of determining estimated blood glucose levels in a biological tissue of a subject using an optical coherence tomography-based monitor comprising a sensor and at least one algorithm, the method comprising the steps of:
   (a) selecting a wavelength of light for which $\mu_a$, an absorption coefficient of the biological tissue, is small relative to $\mu_s$, a scattering coefficient of the tissue for the selected wavelength of light;
   (b) repeatedly scanning a two-dimensional surface area of the biological tissue and interferometrically scanning in a depth dimension with the light during a time period;
   (c) averaging data obtained during scanning to generate a plurality of optical coherence tomography scan data lines, wherein an x-axis of each optical coherence tomography scan data line is depth and a y-axis of each optical coherence tomography scan data line is intensity;
   (d) calibrating an optical coherence tomography-based sensor against at least two invasively obtained blood glucose measurements taken during the time period using the averaged data obtained in step (c), wherein the step of calibrating the optical coherence tomography-based sensor comprises:
      (i) generating a calibration set of estimated blood glucose values by:
         a. selecting the at least first and second invasively obtained blood glucose measurements obtained over the time period, wherein the at least two measurements are spaced apart by a concentration value of at least about 40 mg/dL;
         b. selecting first and second optical coherence tomography scan data lines, corresponding with the first and second invasively obtained blood glucose measurements;
         c. computing intensity differences between the two selected optical coherence tomography scan data lines by subtracting a first baseline scan data line (n) from a second, subsequent optical coherence tomography scan data line (n+1) at every point along the two selected optical coherence tomography scan data lines to generate an intensity difference plot; and
         d. using the intensity difference plot to determine a multitude of offsets and a multitude of intervals to construct a glucose vector grid comprising a multitude of offset, interval pairs; and
      (ii) applying the calibration set to calibrate an optical coherence tomography-based monitor; and
   (e) allowing the calibrated optical coherence tomography-based sensor and at least one algorithm to determine an estimated blood glucose level in the biological tissue.

2. The method according to claim 1, wherein the wavelength of light in step (a) is within the range of about 770 nm to about 1400 nm.

3. The method according to claim 1, wherein in step (d) the optical coherence tomography-based monitor is calibrated by a programmable computer.

4. The method according to claim 1, wherein the glucose vector grid in step (d) further comprises a percentage change value corresponding to each offset, interval pair.

5. The method according to claim 4, wherein the method to obtain the percentage change value for each offset, interval pair comprises the steps:
   (i) calculating a first slope value for a line segment from the first baseline scan data line and a second slope value for a line segment from the second, subsequent optical coherence tomography scan data line for each potential offset and interval pair; and (ii) calculating the difference between the first slope value and the second slope value for each potential offset and interval pair to obtain a percentage change value for each potential offset and interval pair.

6. The method according to claim 1, further comprising the steps:

(f) determining a scattering coefficient proportional to a slope of each optical coherence tomography scan data line for each potential offset, interval pair;

(g) creating a calibration curve correlating scattering coefficients and blood glucose values by performing a regression analysis, wherein each x-value comprises a scattering coefficient corresponding to the scattering coefficient of an invasively obtained blood glucose measurement and each y-value comprises the blood glucose value measured from each invasively obtained blood glucose measurement;

(h) calculating a set of estimated blood glucose values from the scattering coefficients for each potential offset, interval pair;

(i) refining the set of estimated blood glucose values;

(j) averaging the sets of estimated blood glucose values for each point in time to generate the calibration set; and (k) applying the calibration set and selected offset, interval pairs to all subsequent optical coherence tomography scans.

7. The method according to claim 6, wherein refining step (i) further comprises the step (i) applying at least one statistical filter.

8. The method according to claim 7, wherein the statistical filter refines a set of average estimated blood glucose values from each potential offset, interval pair by ignoring sets of estimated blood glucose values that are outside one standard deviation of the set of average estimated blood glucose values at any point in time.

9. The method according to claim 7, wherein the statistical filter refines a set of median estimated blood glucose values by ignoring sets of estimated blood glucose values that are outside one standard deviation of the set of median estimated blood glucose values at any point in time.

10. The method according to claim 7, wherein prior to generating the calibration set of estimated blood glucose values, the at least one statistical filter eliminates negative estimated blood glucose values.

11. The method according to claim 7, wherein prior to generating the calibration set of estimated blood glucose values, the at least one statistical filter eliminates estimated blood glucose values of less than about 10 mg/dL.

12. The method according to claim 7, wherein prior to generating the calibration set of estimated blood glucose values, the at least one statistical filter eliminates high estimated blood glucose values.

13. The method according to claim 7, wherein prior to generating the calibration set of estimated blood glucose values, the at least one statistical filter operates in accordance with the equation (1)

$$BG_{Avg.} - A*BG_{Avg.\ S.D} \leq BG \leq BG_{Avg.} + A*BG_{Avg.\ S.D.} \quad (1)$$

wherein:

$BG_{Avg.}$ is a computed average predicted blood glucose level at a point in time;

$BG_{Avg.\ S.D.}$ is a computed standard deviation of a set of averaged predicted blood glucose levels;

BG is a particular predicted blood glucose level at any point in time; and

A is a filter variable with a range of about 0.1 to about 1.

14. The method according to claim 7, wherein prior to generating a calibration set of estimated blood glucose values, the at least one statistical filter operates in accordance with the equation (2)

$$BG_{Median} - A*BG_{Median\ S.D.} \leq BG \leq BG_{Median} + A*BG_{Median\ S.D.} \quad (2)$$

wherein:

$BG_{Median}$ is a computed median predicted blood glucose level at a point in time;

$BG_{Median.\ S.D.}$ is a computed standard deviation of a set of median predicted blood glucose levels;

BG is a particular predicted blood glucose level at any point in time; and

A is a filter variable with a range of about 0.1 to about 1.

15. The method according to claim 1, step (d) further comprising the steps:

(i) identifying at least one data point in the intensity difference plot where intensity is 0, at least one data point having a maximum intensity surrounding the at least one data point where intensity is 0, and at least one data point having a minimum intensity surrounding the at least one data point where intensity is 0; and (ii) identifying a potential offset range, wherein a first boundary of the potential offset range is the at least one data point having a maximum intensity surrounding the at least one data point where intensity is 0 and a second boundary of the potential offset range is the at least one data point having a minimum intensity surrounding the at least one data point where intensity is 0.

16. The method according to claim 1, wherein the time period includes a blood glucose altering event.

17. The method according to claim 16, wherein the blood glucose altering event is administering insulin.

18. The method according to claim 16, wherein the blood glucose altering event is eating a meal.

19. The method according to claim 16, wherein the blood glucose altering event is drinking a beverage containing sugar.

20. The method according to claim 1, further comprising the steps:

(f) enhancing at least one discontinuity in each selected optical coherence tomography scan data line; and (g) using the at least one discontinuity to generate potential offsets of the multitude of offset, interval pairs.

21. The method according to claim 20, step (f) further comprising the step:

(i) generating a second derivative plot of the optical coherence tomography scan data line.

22. The method according to claim 20, further comprising the step of identifying potential offsets of the multitude of offset, interval pairs by using the at least one discontinuity.

23. The method according to claim 20, wherein the at least one discontinuity indicates potential offsets that correlate closely to locations of a tissue interface transition.

24. The method according to claim 23, wherein the tissue interface transition is a blood vessel.

25. The method according to claim 20, wherein the discontinuity corresponds to changes in blood glucose levels.

26. A noninvasive method of determining estimated blood glucose levels in a biological tissue of a subject using an optical coherence tomography-based monitor comprising a sensor and at least one algorithm, the method comprising the steps of:

(a) selecting a wavelength of light for which $\mu_a$, an absorption coefficient of biological tissue, is small relative to $\mu_s$, a scattering coefficient of the tissue for the selected wavelength of light;

(b) repeatedly scanning a two-dimensional surface area of the biological tissue and interferometrically scanning in a depth dimension with the light during a time period;

(c) averaging data obtained during scanning to generate a plurality of optical coherence tomography scan data lines, wherein an x-axis of each optical coherence tomography scan data line is depth and a y-axis of each optical coherence tomography scan data line is intensity;

(d) calibrating an optical coherence tomography-based sensor against at least two invasively obtained blood glucose measurements taken during the time period using averaged data obtained in step (c), wherein the step of calibrating the optical coherence tomography-based sensor comprises:

(i) using a Pearson's plot to calibrate the optical coherence tomography-based sensor against the at least two invasively obtained blood glucose measurements taken during the time period; and (ii) using Pearson's correlation to maximize correlation between data received from an optical coherence tomography-based monitor and the invasively obtained glucose measurements; and (e) allowing the calibrated optical coherence tomography-based sensor and at least one algorithm to determine an estimated blood glucose level in the biological tissue.

27. The method according to claim 26, wherein the Pearson's plot in step (i) requires at least seven blood glucose measurements invasively obtained over the time period.

28. A method for calibrating an optical coherence tomography (OCT) sensor by correlating OCT measurements with blood glucose measurements, comprising:

taking a plurality of blood glucose measurements from a subject over a specified time period;

obtaining OCT measurements from biological tissue of the subject such that at least one OCT measurement is associated with each blood glucose measurement, each of the OCT measurements capable of being represented as a plot of intensity against depth of the biological tissue;

selecting at least one portion of each of the OCT measurements that includes a selected depth, the selected portion of the OCT measurements correlating with the associated blood glucose measurements, wherein the step of selecting at least one portion of each of the OCT measurements comprises:

(a) computing intensity differences between at least two of the obtained OCT measurements at corresponding depths to generate an intensity difference plot; and (b) using the intensity difference plot to obtain the selected portion and the selected depth of the OCT measurements;

establishing a calibration relationship for an OCT sensor using the selected portions of the OCT measurements and the associated blood glucose measurements; and using a processor, calibrating the OCT sensor with the calibration relationship.

29. The method of claim 28, wherein the step of using the intensity difference plot comprises identifying regions of the OCT measurements that have large changes in intensity.

30. The method of claim 28, wherein the step of using the intensity difference plot comprises identifying regions where intensity differences correlate with blood glucose level changes.

31. The method of claim 28, wherein the step of using the intensity difference plot comprises identifying regions where intensity differences correlate with blood vessels.

32. The method of claim 28, wherein the step of using the intensity difference plot comprises using data of the intensity difference plot corresponding to a peak-to-valley pattern to obtain the selected portion and the selected depth of the OCT measurements.

33. The method of claim 28, wherein the step of using the intensity difference plot comprises identifying a multitude of selected portions and selected depths for the OCT measurements.

34. The method of claim 33, wherein the step of identifying the multitude of selected portions and selected depths comprises constructing a glucose vector grid, an entry of the glucose vector grid being associated with a measure of a change in a slope between two OCT measurements at one selected portion and one selected depth.

35. A method for calibrating an optical coherence tomography (OCT) sensor by correlating OCT measurements with blood glucose measurements, comprising:

taking a plurality of blood glucose measurements from a subject over a specified time period;

obtaining OCT measurements from biological tissue of the subject such that at least one OCT measurement is associated with each blood glucose measurement, each of the OCT measurements capable of being represented as a plot of intensity against depth of the biological tissue;

selecting at least one portion of each of the OCT measurements that includes a selected depth, the selected portion of the OCT measurements correlating with the associated blood glucose measurements, wherein the step of selecting at least one portion of each of the OCT measurements comprises:

(a) enhancing at least one discontinuity in data associated with an obtained OCT measurement; and (b) using the at least one discontinuity to identify the selected depth;

establishing a calibration relationship for an OCT sensor using the selected portions of the OCT measurements and the associated blood glucose measurements; and using a processor, calibrating the OCT sensor with the calibration relationship.

36. The method of claim 35, wherein the step of enhancing at least one discontinuity comprises generating a second derivative plot from the obtained OCT measurements.

37. The method of claim 35, wherein the at least one discontinuity correlates closely with a location of a tissue interface transition.

38. The method of claim 37, wherein the tissue interface transition is a blood vessel.

39. The method of claim 35, wherein the at least one discontinuity corresponds to changes in blood glucose levels.

40. The method of claim 35, further comprising:

constructing a glucose vector grid using at least one identified selected depth.

41. A method for calibrating an optical coherence tomography (OCT) sensor by correlating OCT measurements with blood glucose measurements, comprising:

taking a plurality of blood glucose measurements from a subject over a specified time period;

obtaining OCT measurements from biological tissue of the subject such that at least one OCT measurement is associated with each blood glucose measurement, each of the OCT measurements capable of being represented as a plot of intensity against depth of the biological tissue;

selecting at least one portion of each of the OCT measurements that includes a selected depth, the selected portion of the OCT measurements correlating with the associated blood glucose measurements, wherein the step of selecting at least one portion of each of the OCT measurements comprises:

(a) creating a Pearson plot to indicate correlations between a plurality of OCT measurements at a plurality of portions and depths of the OCT measurements; and (b) using the Pearson plot to select the at least one portion of the OCT measurements and the selected depth;

establishing a calibration relationship for an OCT sensor using the selected portions of the OCT measurements and the associated blood glucose measurements; and using a processor, calibrating the OCT sensor with the calibration relationship.

\* \* \* \* \*

UNITED STATES PATENT AND TRADEMARK OFFICE
CERTIFICATE OF CORRECTION

| | |
|---|---|
| PATENT NO. | : 7,822,452 B2 |
| APPLICATION NO. | : 11/403635 |
| DATED | : October 26, 2010 |
| INVENTOR(S) | : Schurman et al. |

Page 1 of 1

It is certified that error appears in the above-identified patent and that said Letters Patent is hereby corrected as shown below:

At column 4, line 64, change "thereof," to --thereof;--.

At column 15, line 25, change "Us" to --$\mu_s$--.

At column 20, line 22, change "$BG_{Avg.}-A*BG_{Avg.S.D.}\leqq BG \leqq BG_{Avg.}+A*BG_{Avg.S.D.}$" to --$BG_{Avg.} - A*BG_{Avg.S.D.}\leq BG \leq BG_{Avg.}+A*BG_{Avg.S.D.}$--.

At column 25, line 61 (approx.), change "$BG_{Avg.}-A*BG_{Avg.S.D.}\leqq BG \leqq BG_{Avg.}+A*BG_{Avg.S.D.}$" to --$BG_{Avg.} - A*BG_{Avg.S.D.}\leq BG \leq BG_{Avg.}+A*BG_{Avg.S.D.}$--.

At column 26, line 14, in Claim 14, change "$BG_{Median.}$" to --$BG_{Median}$--.

Signed and Sealed this
Twenty-sixth Day of July, 2011

David J. Kappos
*Director of the United States Patent and Trademark Office*